United States Patent
Friedman et al.

(10) Patent No.: US 10,441,457 B2
(45) Date of Patent: Oct. 15, 2019

(54) DEVICES, SYSTEMS AND METHODS FOR THE TREATMENT OF SLEEP APNEA

(71) Applicant: LUMEN DEVICES LLC, Greenwich, CT (US)

(72) Inventors: Michael Friedman, Lincolnwood, IL (US); John N. Irwin, III, Stamford, CT (US); William J. Gorman, S. Hamilton, MA (US); John T. Garibotto, Marblehead, MA (US); J. Christopher Flaherty, Topsfield, MA (US)

(73) Assignee: Lumen Devices LLC, Greenwich, CT (US)

( * ) Notice: Subject to any disclaimer, the term of this patent is extended or adjusted under 35 U.S.C. 154(b) by 0 days.

(21) Appl. No.: 14/818,914

(22) Filed: Aug. 5, 2015

(65) Prior Publication Data

US 2015/0342779 A1    Dec. 3, 2015

Related U.S. Application Data

(63) Continuation of application No. 13/130,869, filed as application No. PCT/US2009/065923 on Nov. 25, 2009, now Pat. No. 9,132,028.

(Continued)

(51) Int. Cl.
*A61F 5/56* (2006.01)
*A61M 16/08* (2006.01)
(Continued)

(52) U.S. Cl.
CPC ............... *A61F 5/566* (2013.01); *A61B 1/00* (2013.01); *A61B 1/233* (2013.01); *A61B 1/267* (2013.01);
(Continued)

(58) Field of Classification Search
CPC .... A61F 5/00; A61F 5/56; A61F 5/566; A61F 5/58; A61B 5/00; A61B 5/48;
(Continued)

(56) References Cited

U.S. PATENT DOCUMENTS 3,132,647 A * 5/1964 Corniello ................ A61F 5/566
128/848
4,669,459 A * 6/1987 Spiewak ................. A61F 5/566
128/848

(Continued)

FOREIGN PATENT DOCUMENTS

| EP | 0418391 | 3/1991 |
|---|---|---|
| EP | 2205306 | 7/2010 |
| WO | 2007020197 A2 | 2/2007 |

OTHER PUBLICATIONS

Supplemental European Search Report dated Feb. 5, 2013 corresponding to European Application No. 09832364.5, 7 pages.

(Continued)

*Primary Examiner* — Victoria J Hicks
(74) *Attorney, Agent, or Firm* — Onello & Mello, LLP.

(57) ABSTRACT

A medical appliance for the treatment of one or more sleep disorders such as obstructive sleep apnea in a patient, the appliance comprising: a biasing member for inserting behind and exerting a force upon the patient's soft palate or tongue, wherein the biasing member is inserted in a reduced or minimized form and then expanded or firms once in place to exert the force. The appliance may be nasally inserted or be placed through the mouth. In a particular configuration, both the soft palate and tongue are biased to prevent obstruction of the flow of air in the nasopharyngeal airway.

8 Claims, 25 Drawing Sheets

Related U.S. Application Data

(60) Provisional application No. 61/209,635, filed on Mar. 9, 2009, provisional application No. 61/203,758, filed on Dec. 29, 2008, provisional application No. 61/200,172, filed on Nov. 25, 2008.

(51) Int. Cl.

| | | |
|---|---|---|
| *A61B 1/233* | (2006.01) | |
| *A61M 16/04* | (2006.01) | |
| *A61F 5/00* | (2006.01) | |
| *A61B 1/00* | (2006.01) | |
| *A61M 16/20* | (2006.01) | |
| *A61B 1/267* | (2006.01) | |
| *A61M 16/00* | (2006.01) | |

(52) U.S. Cl.
CPC .............. *A61F 5/00* (2013.01); *A61F 5/56* (2013.01); *A61M 16/021* (2017.08); *A61M 16/04* (2013.01); *A61M 16/0461* (2013.01); *A61M 16/0463* (2013.01); *A61M 16/0465* (2013.01); *A61M 16/0468* (2013.01); *A61M 16/0488* (2013.01); *A61M 16/0497* (2013.01); *A61M 16/08* (2013.01); *A61M 16/20* (2013.01)

(58) Field of Classification Search
CPC ............ A61B 5/4806; A61B 5/4818; A61M 2025/1081; A61M 2025/1043; A61M 2025/0079; A61M 25/10; A61M 25/0155; A61M 25/1018; A61M 25/10181; A61M 25/10183; A61M 25/00; A61M 25/10187; A61M 25/10186; A61M 25/10184; A61M 25/10185; A61M 29/00; A61M 29/02; A61M 39/00; A61M 2025/1047; A61M 25/1002; A61M 2025/1004; A61M 25/1006; A61M 25/1011
USPC .. 128/846, 848, 857, 859–860, 863, 200.14, 128/200.15; 602/902
See application file for complete search history.

(56) References Cited

U.S. PATENT DOCUMENTS

| | | | |
|---|---|---|---|
| 4,883,465 A | 11/1989 | Brennan | |
| 5,103,807 A | 4/1992 | Makaran | |
| 5,938,582 A * | 8/1999 | Ciamacco, Jr. | A61N 5/1002 600/3 |
| 6,117,386 A * | 9/2000 | Stiger | A61M 25/0021 264/526 |
| 6,394,093 B1 | 5/2002 | Lethi | |
| 6,408,852 B2 * | 6/2002 | Tielemans | 128/848 |
| 6,605,056 B2 | 8/2003 | Eidenschink | |
| 8,127,769 B2 * | 3/2012 | Walker | A61F 5/566 128/848 |
| 8,302,609 B2 * | 11/2012 | Martinez | A61F 5/566 128/848 |
| 8,684,007 B2 * | 4/2014 | Timmons | A61F 5/566 128/848 |
| 8,739,794 B2 * | 6/2014 | Cutler | A61F 5/566 128/207.14 |
| 2001/0027793 A1 * | 10/2001 | Tielemans | A61F 5/56 128/848 |
| 2003/0014007 A1 * | 1/2003 | Eidenschink | A61M 25/104 604/96.01 |
| 2004/0020492 A1 | 2/2004 | Dubrul et al. | |
| 2004/0049102 A1 | 3/2004 | Nelson et al. | |
| 2004/0194785 A1 | 10/2004 | Miller | |
| 2005/0240147 A1 | 10/2005 | Makower et al. | |
| 2005/0268919 A1 | 12/2005 | Knudson et al. | |
| 2006/0106361 A1 * | 5/2006 | Muni | A61B 5/411 604/500 |
| 2006/0130850 A1 | 6/2006 | Chen | |
| 2006/0169285 A1 | 8/2006 | Bovo | |
| 2006/0195135 A1 * | 8/2006 | Ayoub | A61M 25/10 606/192 |
| 2007/0129751 A1 | 6/2007 | Muni et al. | |
| 2008/0041396 A1 * | 2/2008 | Lucker | A61F 5/566 128/845 |
| 2008/0065209 A1 | 3/2008 | Pflueger | |
| 2008/0091067 A1 | 4/2008 | Dollar | |
| 2008/0210244 A1 | 9/2008 | Keropian | |
| 2008/0289637 A1 | 11/2008 | Wyss | |
| 2010/0198249 A1 * | 8/2010 | Sabliere | A61F 5/0089 606/192 |

OTHER PUBLICATIONS

Office Action dated Aug. 29, 2013 corresponding to Australian Patent Application No. 2009324904, 3 pages.
European Office Action dated Jul. 3, 2014 corresponding to European Patent App. No. 09832364.5-1654, 4 pages.
Canadian Office Action dated Aug. 13, 2014 corresponding to Canadian Patent App. No. 2744704, 3 pages.
Extended European Search Report dated Jun. 20, 2016 issued in corresponding European Application No. 15195168.8.
Canadian Office Action dated Sep. 6, 2016 issued in corresponding Canadian application No. 2911748.
Canadian Office Action dated Jun. 6, 2017 issued in related Canadian Application No. 2,911,748.
Canadian Office Action dated Feb. 14, 2018 issued in Canadian Application No. 2,911,748.
European Office Action dated Nov. 8, 2017, issued in Euorpean Application No. 15195168.8.

\* cited by examiner

DEVICES, SYSTEMS AND METHODS FOR THE TREATMENT OF SLEEP APNEA

CROSS-REFERENCE TO RELATED APPLICATIONS

This application is a continuation application of U.S. Ser. No. 13/130,869, filed May 24, 2011, which is a national stage application of PCT Application No. PCT/US09/65923, filed on Nov. 25, 2009, and claims priority to US Provisional Patent Application Nos. 61/200,172, filed on Nov. 25, 2008, 61/203,758, filed on Dec. 29, 2008, and 61/209,635, filed on Mar. 9, 2009, all of which are incorporated herein in their entirety by reference thereto.

BACKGROUND

1. Field

The present disclosure relates generally to the use of nasally and orally inserted devices for the treatment of patients with one or more sleep disorders, such as sleep apnea or severe snoring. The devices are configured to provide a biasing force to the soft palate or the tongue, such that continuous airflow can be achieved while the patient sleeps.

2. Discussion of the Background Art

The sleep apnea syndrome, and in particular obstructive sleep apnea, afflicts an estimated 2-5% of the general population and is due to episodic upper airway obstruction during sleep. Those afflicted with obstructive sleep apnea experience sleep fragmentation and intermittent, complete or nearly complete cessation of ventilation during sleep with potentially severe degrees of oxyhemoglobin unsaturation. These features may be translated clinically into debilitating daytime sleepiness, cardiac disrhythmias, pulmonary-artery hypertension, congestive heart failure and cognitive dysfunction. Other problems related to sleep apnea include carbon dioxide retention during wakefulness as well as during sleep, and continuous reduced arterial oxygen tension. Hypersomnolent sleep apnea patients may be at risk for excessive mortality from these factors as well as from an elevated risk for accidents such as while driving or operating other potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to obstruct the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

One theory of the cause for the sleep disturbance is the relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and posterior walls of the pharynx collapse, causing snoring or more seriously, causing partial or complete obstruction of the airway.

Obstructive sleep apnea occurs due to a collapse of soft tissue within the upper airway during sleep.

Apnea is the term for suspension of breathing. During apnea there is no movement of the muscles of respiration. The ongoing force of inspiration serves to generate increasingly negative pressure within the pharynx, causing further collapse. The lack of respiration results in inadequate blood oxygenation, and rising carbon dioxide levels. The cardiovascular response produces an increase in the blood pressure and pulse. Cardiac arrhythmia's often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at 2-3 APNEAS per hour, and it is not uncommon to find patients with indices of 75 or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Surgical Treatments

The treatment of sleep apnea has included such surgical interventions as Uvulopalatopharyngoplasty (UPPP) gastric surgery for obesity, and maxillo-facial reconstruction. Another mode of surgical intervention used in the treatment of sleep apnea is tracheostomy. These treatments constitute major undertakings with considerable risk of post-operative mortality. In UPPP, any remaining tonsil tissue and a portion of soft palate is removed. The procedure often increases the nasopharyngeal airway. However, UPPP does not always fix a sagging soft palate nor does it address apnea caused by obstructions caused by the base of the tongue being deeper in the oropharynx part of the airway. These surgical techniques are extremely invasive, requiring general anesthesia, and a prolonged, painful recovery.

LAUP, or Laser-Assisted Uvulopalatoplasty, is a modification of the above-mentioned technique, but has had mixed success and cannot solve obstructions behind the base of the tongue.

Radio frequency tissue ablation (RFTA) with the trade name "Somnoplasty", has been used to shrink the soft palate, uvula and reduce tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. More than one session is typically required, and other surgeries may still be necessary in moderate to severe cases, and there are occasional problems with morbidity.

Another area of surgical interest lies in techniques designed to pull the tongue anteriorly. The most recent such surgical system designed to treat snoring (as well as obstructive sleep apnea) was approved by the FDA in February 1998. Known as the tongue suspension procedure (with the trade name Repose), it is intended to pull the tongue forward, thereby keeping the tongue from falling into the airway during sleep. The system utilizes a bone screw inserted into the mandible. The screw attaches to a non-absorbable suture which travels the length of the tongue and back. Similarly, the hyoid bone can be drawn anteriorly with two distinct screws, also attached to the mandible.

Techniques have also been developed for treating, specifically, the condition of snoring. Conrad et al., U.S. Pat. No. 6,250,307 discloses a method for treating snoring of a patient, which includes embedding an implant into a soft palate of a patient in order to alter a dynamic response of a soft palate to airflow. The methods of Conrad et al. are specifically designed to reduce the audibility of snoring but do not address the more serious condition of sleep apnea.

These conventional treatments continue to suffer poor or partial cure rates. The failures lie in their inability to maintain patency in the retropalatal region and retroglossal region (the caudal margin of the soft palate to the base of the epiglottis). The poor success rates combined with high morbidity from some of the surgical interventions, contribute to an ongoing need for more effective treatments for sleep apnea and/or snoring.

Pharmacological Treatments

Pharmacological therapy aimed at stimulating upper airway muscle to reduce apneas also have, in general, been disappointing. In addition, side effects from the pharmacological agents that have been used are frequent. Thus, medical practitioners continue to seek non-invasive modes of treatment for sleep apnea with high success rates and high patient compliance including, for example in cases of minor to moderate sleep apnea relating to obesity, weight loss through a regimen of exercise and regulated diet.

Other Non-Surgical Treatments

Other non-surgical treatments for sleep apnea include the use of oral devices and appliances that work to prevent the tongue from falling backwards or help reduce the collapse of the soft palate. These involve the use of retainers that push the lower jaw forward, thereby pulling the tongue slightly forward and, in some cases, helping elevate the soft palate. Also, there are devices that pull on the tongue to keep it forward during sleep. These current oral devices, typically do not create a significant improvement except in mild to moderate cases and can be associated with movement of the teeth over time of problems with the temporamandibular joint.

Recent work in the treatment of sleep apnea has included the use of continuous positive airway pressure (CPAP) to maintain the airway of the patient in a continuously open state during sleep, CPAP by delivering a stream of air under pressure through the nose or mouth stents the airway (keeping it open) so that apneas are reduced and breathing during sleep becomes unobstructive.

For example, U.S. Pat. No. 4,655,213 and Australian patent AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

Although CPAP has been found to be very effective and well accepted, it suffers from some of the same limitations, although to a lesser degree, as do the surgical options; specifically, a significant proportion of sleep apnea patients do not tolerate CPAP well. Thus, development of other viable non-invasive therapies has been a continuing objective in the art.

Still others have attempted to solve sleep apnea disorders using intraorally fitted appliances, including U.S. Pat. Nos. 4,981,437 and 4,932,867, that disclose a method and apparatus for constructing dentures, which are useful, for example, in treating breathing disorders. U.S. Pat. No. 4,386,405 discloses a device for measuring the location, attitude, or change of location of a patient's lower jaw. U.S. Pat. No. 4,859,181 relates to optical measurement of jaw movement. U.S. Pat. Nos. 3,998,209 and 4,220,142 disclose conditioning systems for use in a program of behavior modification to eliminate snoring, while U.S. Pat. No. 4,976,618 relates to treatment of temporomandibular joint dysfunction and bruxism. U.S. Pat. No. 3,297,021 discloses an intraoral strain gauge and telemetering of information from an intraoral location to an outside indicator.

The following U.S. patents purport to relate to tongue positioning and/or retaining apparatus: U.S. Pat. Nos. 5,154,184, 5,092,346, 5,046,512, 4,676,240, 4,169,473, 4,304,227 and 4,593,686. Other patents addressing the matter of tongue positioning include the following: U.S. Pat. Nos. 5,649,540, 5,465,734, 5,373,859, 5,052,409, 4,715,368, 4,196,724, 3,884,226, 3,312,216 and 3,132,647, as well as European patent 0182387 and British patent 874,480. The following patents purport to relate to chin straps or similar apparatus intended to hold the jaw closed: U.S. Pat. Nos. 3,312,217, 2,711,730 and 1,990,411.

Other patents relate to apparatus for interaction with the soft palate in the user's oral cavity. These include U.S. Pat. Nos. 4,669,459 and 5,316,020, German patent no. DE 40 26 602 and European patent no. EP 0264516. Other patents of general interest include U.S. Pat. Nos. 5,056,534 and 2,705,006, German patent nos. 65194 and 2320501, and PCT publication no. WO 92/05752 and European patent application no. 0 487 469 A1.

While the above-identified conventional devices and surgical techniques are purported to treat upper airway instability, such as OSA or snoring, they are successful, if at all, in only a limited pool of patients or under limited circumstances. While CPAP therapy has had significant success in reducing or eliminating apneas through the delivery of air under pressure, CPAP treatment suffers from patient non-compliance and cannot be tolerated by an ample minority of patients. Therefore, there remains a relatively large number of patients whose airway disorder is believed to be treatable using an intraoral appliance, yet conventional appliances are ineffective, overly burdensome, uncomfortable, or any combination thereof.

The present disclosure overcomes the aforementioned disadvantages of the prior art by using a novel oral appliance that is positioned behind the soft palate and/or tongue and provides for continuous or semi-continuous flow of air through the nasopharynx.

The present disclosure also provides many additional advantages, which shall become apparent as described below.

SUMMARY

A medical appliance for a patient comprising: a securing device attached to a jaw of the patient; and a biasing member connected to the securing device, the biasing member expands and/or contracts to exert a force upon a soft palate and/or base of a tongue of the patient. The biasing member comprises: an expandable member which expands upon introduction of a liquid or gas therein, and a valve which opens or shuts to allow the liquid or gas to enter or exit from the expandable member.

A method for the treatment of sleep apnea comprising: placing a securing device about an upper or lower jaw of a patient; connecting a biasing member to the securing device, the biasing member expands and/or contracts to exert a force upon a soft palate and/or base of a tongue of the patient.

A medical appliance for a patient comprising: a nasal tube; a biasing member either removable disposed within the nasal tube or disposed about a distal end of the nasal tube, wherein the biasing member expands and/or contracts to exert a force upon a soft palate and/or base of a tongue of the patient.

A medical appliance for a patient comprising: a tubular body comprising a proximal end, a distal end and a lumen therethrough; a plunger comprising a plunger head portion; and a biasing member in contact with the plunger head portion; wherein the biasing member is disposed within the tubular body such that is it expelled via the distal end thereof upon activation of the plunger head portion; and wherein the biasing member exerts a force upon a soft palate and/or a base of a tongue of the patient.

A method of inserting an appliance into an oral cavity of a patient, the method comprising: selecting an appliance comprising: a tubular body comprising a proximal end, a distal end and a lumen therethrough; a plunger to comprising a plunger head portion; and a biasing member in contact with the plunger head portion; wherein the biasing member is disposed within the tubular body such that is it expelled via the distal end thereof upon activation of the plunger head portion; and wherein the biasing member exerts a force upon a soft palate and/or a base of a tongue of the patient; placing the end of the tubular body behind a the soft palate and/or base of a tongue of the patient; depressing the plunger and expelling the biasing member behind the soft palate and/or the base of the tongue.

A method for the treatment of sleep apnea comprising: inserting a nasal tube into the nasal passage of a patient, said nasal tube comprising a tube body and a biasing member, wherein said biasing member is either disposed within said tube body or disposed about a distal end portion of said tube body; expanding and/or contracting said biasing member, thereby exerting a force upon a soft palate and/or base of a tongue of said patient.

The biasing member comprises: an expandable member which expands upon introduction of a liquid or gas therein, and a valve which opens or shuts to allow said liquid or gas to enter or exit from said expandable member. Alternatively, the biasing member comprises: an expandable member and an actuator which expands and/or contracts said expandable member. The actuator is either a push or pull wire.

According to a first aspect of the invention, an oral appliance is disclosed, such as a tube or other airway expander or stiffener, that can be placed via the opening of the mouth into the back of the throat behind the soft palate and/or tongue, wherein the tube or other airway expander has itself or creates a lumen large enough to allow for clinically efficacious passage of air in the nasopharynx and behind the tongue. Such tubes or airway expanders add support for one or both sides, as it is not necessarily a full breathing tube, but rather provides added support and stiffness to prevent the occlusive collapse of tissue for those suffering from sleep apnea and other sleeping or breathing disorders. Unlike most oral devices that only indirectly (i.e. pulling the lower jaw forward and therefore bringing the attached tongue slightly forward) treat the problem of collapse of the breathing area in the retropalatal and retrolingual areas (i.e. the area behind the soft palate and the tongue), this oral appliance device directly stents the retropalatal and retrolingual airways with one or more biasing members. These biasing members may apply a full (i.e., 306°) or partial circumferential force to the airway. This treatment can be supplemented with minimally invasive surgical treatments, such as the use of radio frequency aimed at shrinking the tongue, and numerous other procedures applicable to the base of the tongue or the soft palate. However, surgical treatments do not stent open the airway. Furthermore, this oral appliance aims to be placed into the retropalatal and retrolingual areas in a minimal, compacted form that can be expanded once in place or be configured to apply a biasing force to tissue, such as a force achieved by a resiliently biased arm attached to a retainer attached to the patient's jaw, or a magnetic attraction between two elements on either side of the patient's soft palate.

Broadly stated, to provide support for the airway behind the base of tongue, the tubes or airway expanders can be partial tubes or wires bent into a circular or other shapes and positioned behind and far enough below the top of the tongue so that they do not come into contact with the soft palate when the jaw is in the closed position. Such wire or mesh tubes would provide the tongue with partial support by supporting the sides of the tongue. Another embodiment would provide support fully across the base of the tongue by means of a wire mesh stent or other expanding device that can be pushed out from a tube so that it passes across the base of the tongue in the back of the airway. It is contemplated that the present disclosure will include any expander or retainer configuration that minimizes the patient's gag reflex, such as by applying the minimal force necessary to create a sufficient opening for suitable breathing. To minimize any discomfort or disturbance behind the tongue a flexible small tube will be positioned to place an expanding device or stent, or other expandable device—by air or water pressure or by mechanical means—either on both sides of the tongue or across the whole base of the tongue. Alternatively, a small flexible group of wires can be placed behind the tongue made of memory wire or other smart materials that are activated, usually by a temperature transition, to form a pre-determined shape, thereby directly stenting the airway. Wires can be of any shape, size or material and, in addition, may include rods and the like.

Support for an airway behind the soft palate is provided by a semi-tube or the like at a higher plane than the very short tube that protrudes behind the base of the tongue, discussed above. This semi-tube would be a T-shaped tube resting on the top of the tongue and it would be retracted until the semi-tube is in place. Then the T-shaped tube is advanced until it is all the way back behind the soft palate and the semi-tube. This semi-tube is then rotated upwards (i.e., a finger or lever could manipulate the inside back part of the retainer for the rotation, minimizing the gag reflex. Once behind the soft palate, this semi-tube, which itself has numerous air holes, exerts a biasing force on the soft palate, allowing more air to pass thereto. The semi-tube is preferable made from medical grade plastic materials, with C-shaped ribs positions along the length of the tube so that the tube does not collapse in use, while permitting sufficient flexibility for removal without having to rotate the tube downwards after use. In a particular embodiment, the semi-tube or other biasing member can also be moved in an anterior or posterior direction, increasing or decreasing, respectively, the biasing force upon the soft palate and/or tongue. Inadequate force applied to tissue is overcome with anterior movement. Patient discomfort, such as gagging or difficulty swallowing, is reduced with moving the semi-tube in a posterior direction.

Instead of the semi-tube, an alternative design according to yet another embodiment of the present disclosure includes a tube catheter through which a stent can be pushed into place behind the soft palate and/or tongue.

It is desirable to have an oral appliance that is initially compressed so as to allow easy placement behind the soft palate and/or base of the tongue. Such oral appliances will then expand once in place behind the soft palate and/or base of the tongue. Such an oral appliance can be made out of a metal or plastic which changes to a desired shape due to a change in temperature, i.e., expands due to body temperature once in position. In a particular embodiment, a tubular membrane surrounds the biasing member, such as to automatically compress the biasing member when radial expansion force is removed.

According to another aspect of the invention, a medical appliance is disclosed which comprises a nose cone and a nasal tube, a stent or wire configured to pass through the nose, through the nasal passageway and behind the soft plate and/or tongue, wherein the nasal tube comprises at least one stiffener or expander disposed about an end of the nasal tube opposite to that of the nose cone. The expander is typically inserted into and removed from the nasal passageway in a collapsed or non-expanded state. Once in position behind the soft palate and/or tongue the expander is expanded by means of gas or liquid pressure passing through an opening in the nasal tube or by mechanical means, such as a push or pull wire mechanism or any shaped memory metal or polymer activated expander. The expander may apply a full (i.e. 360°) or partial circumferential force to the airway.

In accordance with one embodiment, a plurality of expanders are disposed about the end of the nasal tube, whereby one expander expands during use to provide an air passageway between the soft palate and the nasal pharynx and the other expander provide an air passageway between the back of the tongue and the oral pharynx. The expanders can be selected from one or more inflatable balloons or radially inflatable discs. In one embodiment a plurality of discs are assembled within a mesh outer sack to form an expander and positioned behind either soft palate or tongue. Still yet another embodiment provides for an to expander which comprises a plurality of balloons disposed substantially perpendicular to the nasal tube and encased within a mesh sack. Still yet another embodiment provides for an expander which comprises a single balloon with multiple lobes, such as three or more lobes. Another expander can include a plurality of mechanical expanders that expand outward when a gas such as air, a liquid or mechanical pressure means is applied to the nasal tube, wherein the mechanical expanders are encased within a mesh sack or a resiliently biased membrane, such as a membrane configured to apply a compressive force on the expanders or other biasing members.

A further embodiment according to the present disclosure combines an stiffener or expander device together with a ferrous metal or magnet affixed to the nasal tube, wherein the ferrous metal or magnet is disposed behind the soft palate and a retainer disposed about the upper jaw and palate of a patient includes a corresponding metal or magnet to draw the metal or magnet of the nasal tube toward the retainer, such that the soft palate is pulled away from the back wall of the nasal pharynx region, thereby providing an air passageway.

Still yet another embodiment comprises at least one expander disposed about an end of the nasal tube opposite the nose cone, whereby the expander can be collapsed or expanded by means of either a push or pull wire or other filament. The push or pull wire preferably passes through the nasal tube and is affixed via a retainer or fastener at the opposite end of the nasal tube.

A novel nasal tube with a nasophryngeal stiffener or expander that fits behind the soft palate with a tube or other airway extender that stents the airway to allow for the passage of air in the nasopharynx and behind the tongue is also disclosed.

Yet another embodiment comprises two nasal tubes disposed on either to side of the soft palate and/or tongue, preferably held behind the soft palate, and configured to allow for easier swallowing and patient comfort.

According to yet another aspect of the invention, an orally inserted appliance is disclosed comprising a hollow carrier tube, a plunger, a plunger head portion, an expander disposed in contact with plunger head portion, a cap movably secured to an end portion of plunger, a retainer connected by wire or tube to expander, and carrier tube mounts disposed about an exterior surface of tube for mounting retainer to tube. Advancement of the plunger head portion causes the expander to be ejected from the tube. In one embodiment, the expander comprises a collapsible or bendable wire or tube having at least one expandable balloon or mesh ball disposed thereupon such that in the expanded state, lumens or other open shapes maintain one or more openings in the air passageway behind soft palate and tongue, such as to achieve a clinically efficacious passage of air. The force applied may be a full (i.e. 360°) or partial circumferential force to the airway.

In a particular embodiment, the biasing member can also be moved in an anterior or posterior direction, increasing or decreasing, respectively, the biasing force upon the soft palate and/or tongue. Inadequate force applied to tissue is overcome with anterior movement. Patient discomfort, such as gagging or difficulty swallowing, is reduced with moving the semi-tube in a posterior direction. In another embodiment, a tubular membrane surrounds the biasing member, such as to automatically compress the biasing member when radial expansion force is removed.

The appliances of the present disclosure target expansion by applying biasing force or forces only where needed to stent or otherwise provide flow passageways within the patient's airways, thereby reducing discomfort for the user by eliminating or reducing undesired, or unnecessary applied force. In a particular embodiment, tissue contact is avoided in the posterior half of the cylinder defining the patient's airway. Tissue contact in the anterior portion of the patient's airway can be applied to portions 180° or less, such as portions less than 180° to minimize patient discomfort such as involuntary or difficulty swallowing, as well as triggering of the gag reflex.

Another embodiment according to the present disclosure includes a collapsible wire or tube having an expandable ball disposed at one end thereof to maintain an airway behind the base of the tongue and a pair of magnets disposed about the soft palate or a magnet and a material able to be attracted to the magnet. One magnet is connected or is part of the retainer that fits in front of the soft palate and the other magnet or material that is attracted to the magnet is attached to the tube or wire that has been placed behind the soft palate. The magnet causes the magnet disposed on a side of the soft palate opposite thereto to ensure that the soft palate is pulled toward the oral cavity, thereby maintaining an air passageway behind the soft palate.

In operation, a patient will insert the oral appliance into their oral cavity, slightly depressing the tongue and fitting it just behind the soft palate on one side of the uvula. The patient will then push the plunger forward such that the expander is expelled from the plunger device and expands upward behind the soft palate and/or downward behind the base of the tongue. In one embodiment, as the plunger is moved toward the back of the oral cavity, a triangular-shaped end cap on the plunger tube is opened by the force applied by the plunger, such that the cap is opened via a hinge or the like and the expander is dislodged from the tube. As force is applied to the soft palate, the retainer is dislodged from the outer surface of the plunger and secured to the upper jaw of the patient, thereby ensuring that the expander remains in a proper position in the patient's throat due to the attachment between the inside edge of the retainer and expander. The expander can be attached to an air tube to allow for air to be used to expand the expandable biasing members, although other mechanical, heat or electrical activation means of expanding expander balls or other expandable elements known to one of ordinary skill in the art are also contemplated herein.

For example, a tiny air tube can be attached to the middle of the tube expander tube and routed back through the retainer, which then is designed to receive an air tube from an outside air source.

As an alternative to the expander balls, the present disclosure also contemplates expanding using other technologies, such as expandable wire mesh balls, temperature sensitive or electrically activated memory metals or plastics, air or liquid inflated balloons such as multi-lobed balloons, micromuscles, pneumatic artificial muscles, or muscular thin films all of which would enlarge or change shape to stent or otherwise apply force to appropriate tissue to prevent occlusion of the airway.

According to another aspect of the invention, a medical appliance includes one or more biasing members configured to apply a force to patient tissue behind the soft palate or base of the tongue. The biasing member includes one or more expandable members, such as balloons or other inflatable devices. A removably attached fill assembly is configured to be squeezed or otherwise compressed to propel a gas such as air or a liquid such as saline through an inflation lumen and into the biasing member. A valve is included to maintain the pressure in the biasing member if the fill assembly is removed. The valve can be removed to evacuate the biasing member prior to removal. In one embodiment, a resiliently biased membrane surrounds the expandable biasing member to cause or otherwise assist in the evacuation of the pressurizing gas or liquid.

Further objects, features and advantages of the present disclosure will be understood by reference to the following drawings and detailed description.

DETAILED DESCRIPTION OF THE PREFERRED EMBODIMENT

Figure 23:
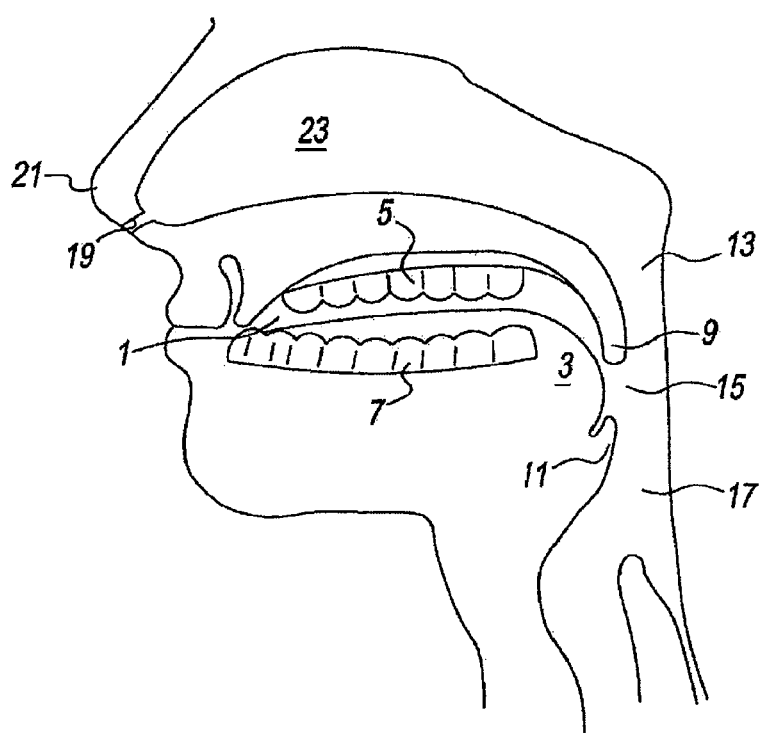
FIG. 23 is a cross-sectional view of the oral and nasal cavities of a patient.

The present disclosure can best be described by referring to the figures, wherein FIG. 23 shows a cross-section of a patient's oral cavity 1. Oral cavity 1 includes a tongue 3, upper jaw 5, lower jaw 7, soft palate 9, and epiglottis 11, as well as the nasopharynx region 13, oropharynx region 15 and laryngopharynx region 17. In addition, nasal valve 19 and nose 21 having a nasal passageway 23 to connect nasal valve 19 with nasopharynx region 13.

Figure 1:
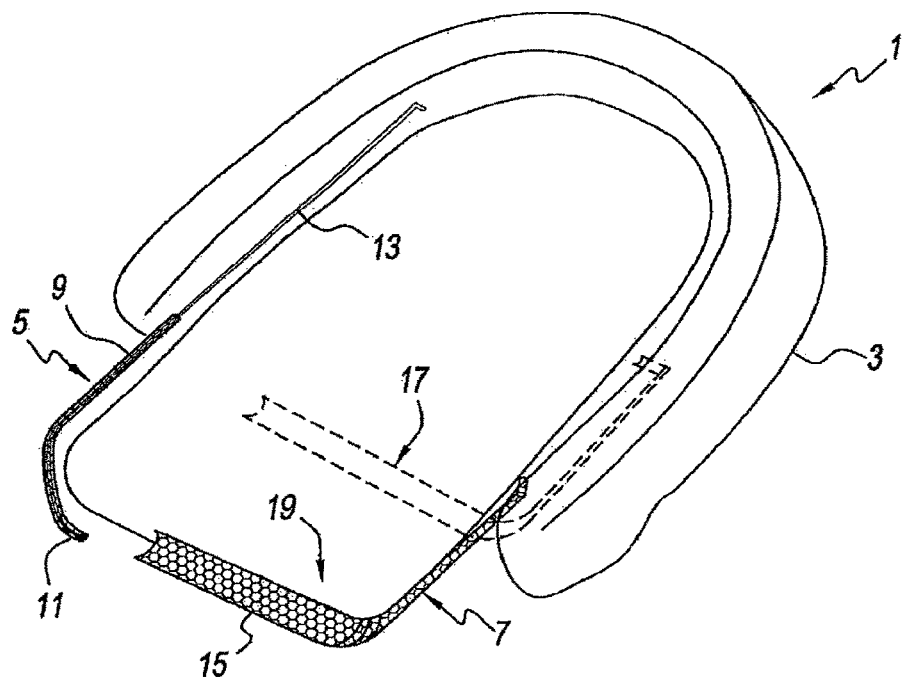
FIG. 1 is a front top perspective view of an oral appliance according to one embodiment of the present disclosure, wherein the soft palate wire mesh retainer and tongue cylinder retainer are in the insertion position.

Referring now to FIG. 1, an oral appliance 1 according to a first embodiment of the present disclosure is disclosed, comprising a molded retainer 3 which is designed to fix securely about a patient's teeth in the lower jaw, thereby securing appliance 1 to the patient's jaw. Alternatively, retainer 3 can be designed such that it is only disposed about a portion of the teeth rather than the entire lower or upper jaws.

For example, one side of the jaw could hold a retainer with a device aimed at supporting the soft palate and the other side of the jaw could hold a retainer designed to support the base of the tongue for ease of insertion and retraction. A tongue retainer assembly 5 and soft palate retainer assembly 7 are affixed to opposite sides of molded retainer 3. As shown in FIG. 1, tongue retainer assembly 5 comprises an elongated tube 9 with an expandable mesh to cylinder 11 disposed about one end thereof. Expandable mesh cylinder 11 is actuated via push rod 13. Soft palate retainer assembly 7 is preferably formed of a mesh tubing, wherein the outer portion 15 thereof is preferably a half tube. FIG. 1 shows soft palate retainer assembly 7 in a phantom view to depict how it move from its initial position 17 to its insertion position 19, wherein insertion position 19 ensures that outer portion 15 is disposed behind the soft palate of a patient. In a preferred embodiment, insertion position 19 can be further adjusted, such as to increase or decrease the force applied to tissue of the patient's airway. Increased force may be necessary to provide a significant airflow during patient's breathing. A decrease in force may be needed for patient's comfort, such as to accommodate swallowing or avoid a gag reflex.

Figure 2:
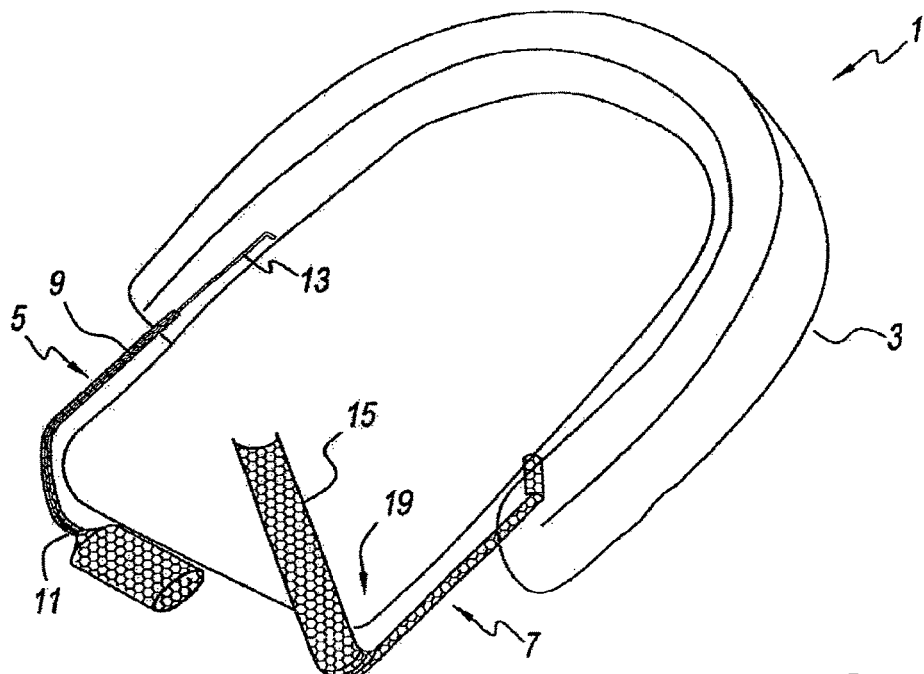
FIG. 2 is a front top perspective view of the medical application according to FIG. 1, wherein the soft palate retainer has been directed upwards and the tongue retainer has been expanded by a push method such that they are both in their active retention positions.

FIG. 2 depicts oral appliance 1, as shown in FIG. 1, wherein soft palate retainer assembly 7 is rotated into the active position, such that outer portion 15 is disposed perpendicular to retainer 3 and behind the soft palate of a patient, not shown. Expandable mesh cylinder 11 has been pushed out of elongated tube 9 via push rod 13 and is in the expanded position behind the tongue.

Figure 3:
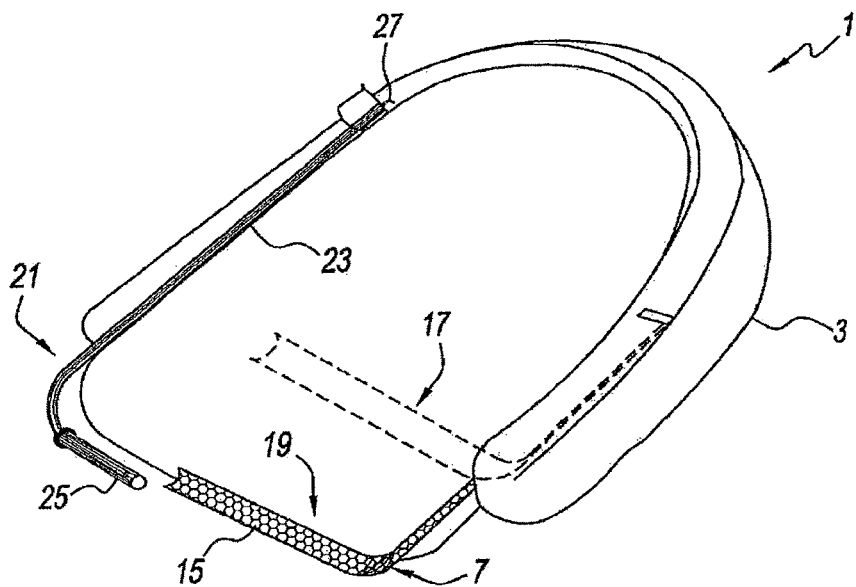
FIG. 3 is a front top perspective view of an oral appliance according to one embodiment of the present disclosure, wherein the soft palate wire mesh retainer and tongue bulb retainer are in the insertion position.
Figure 4A:
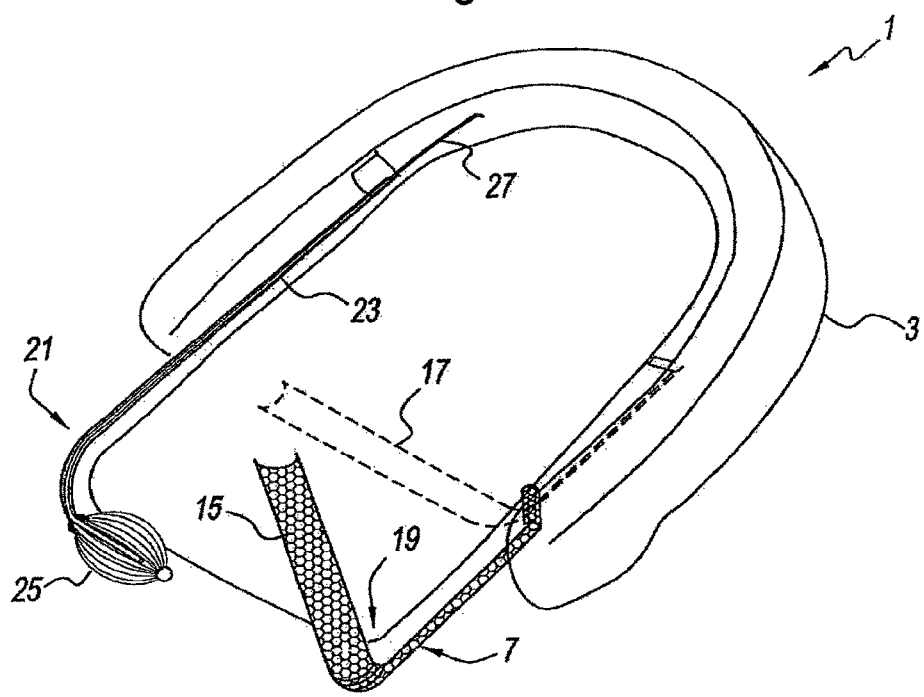
FIG. 4a is a front top perspective view of the oral appliance according to FIG. 3, wherein the soft palate retainer has been directed upwards and the tongue retainer has been expanded by a pull method such that they are both in their active retention positions.

FIGS. 3 and 4a are similar to FIGS. 1 and 2, except that tongue retainer assembly 21 is a pull bulb configuration, wherein assembly 21 comprises a elongated tube 23, bulb 25 and pull wire or rod 27. Alternatively, bulb 25 can be expanded via heat actuatable memory wire or shaped memory plastics rather than being mechanically controlled via a pull or push mechanism. In particular, FIG. 3 depicts bulb 23 in the collapse position during insertion and FIG. 4a shows bulb 23 in the expanded position during use.

Figure 8:
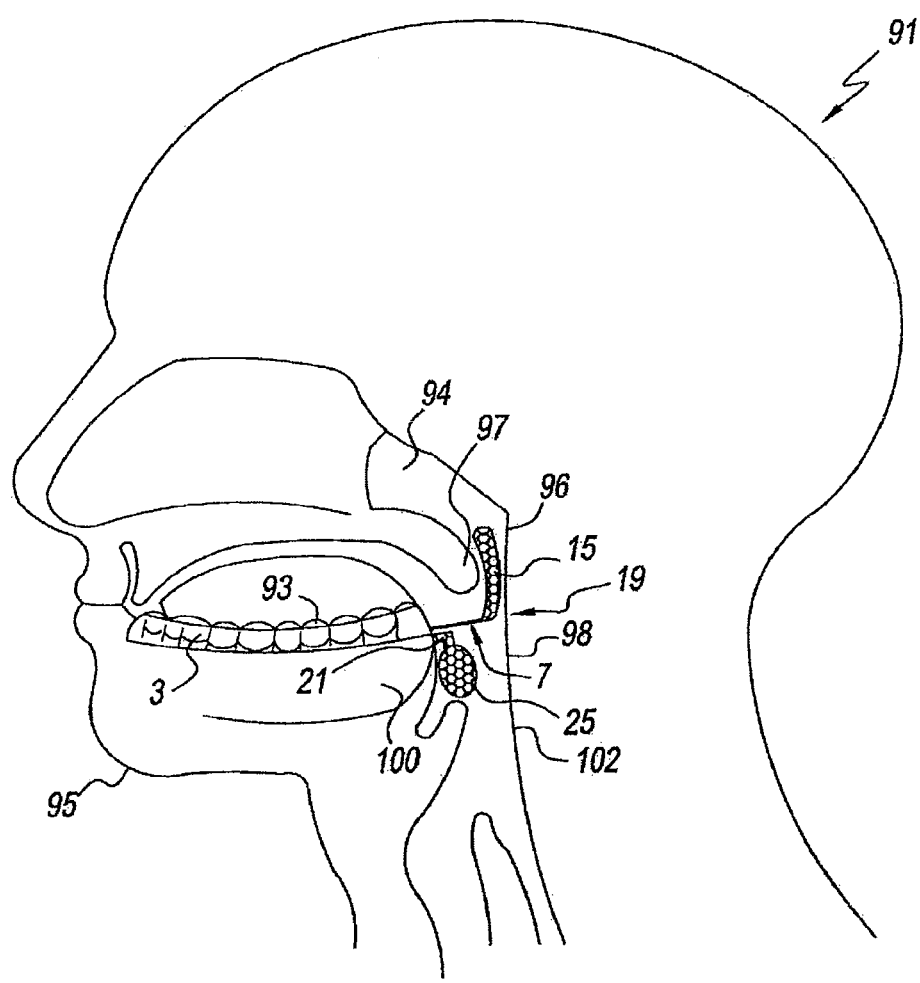
FIG. 8 is a cross-sectional view of a patient having an oral appliance according to the present disclosure, wherein a tongue bulb retainer is expanded to retain the tongue and an upwardly positioned expandable soft palate retainer is positioned to retain the soft palate, thereby providing an air passageway therebetween.

FIG. 8 shows a patient 91 having a retainer 3 similar to that shown in FIGS. 3 and 4a, wherein retainer 3 is disposed about teeth 93 of lower jaw 95. Retainer 3 includes a tongue retainer assembly having an elongated tube 21 and expanded bulb 25 and a soft palate assembly 7 having outer portion 15 disposed perpendicular to retainer 3 and behind soft palate 97 of patient 91. Outer portion 15 is configured to allow air to flow from the nasal passageway 94 through nasopharynx region 96 and into the oropharynx region 98. Bulb 25 prevents or substantially reduces tongue 100 from blocking the air flowing through oropharynx region 98 and laryngopharynx region 102. Alternatively, bulb 25 can be replaced with a mesh stent or electrically activated shaped memory wire (e.g. Nitinol) or shaped memory plastic material.

Figure 4B:
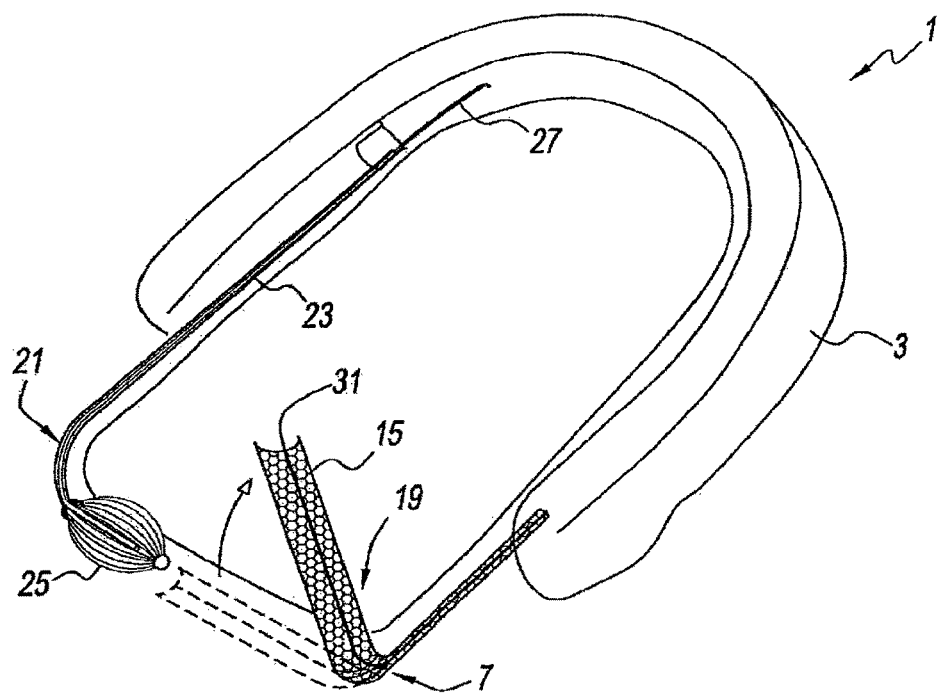
FIG. 4b is a front top perspective view of the oral appliance according to FIG. 3, wherein the soft palate retainer has been directed upwards via a memory wire and the tongue retainer has been expanded by a pull method such that they are both in their active retention positions.
Figure 4C:
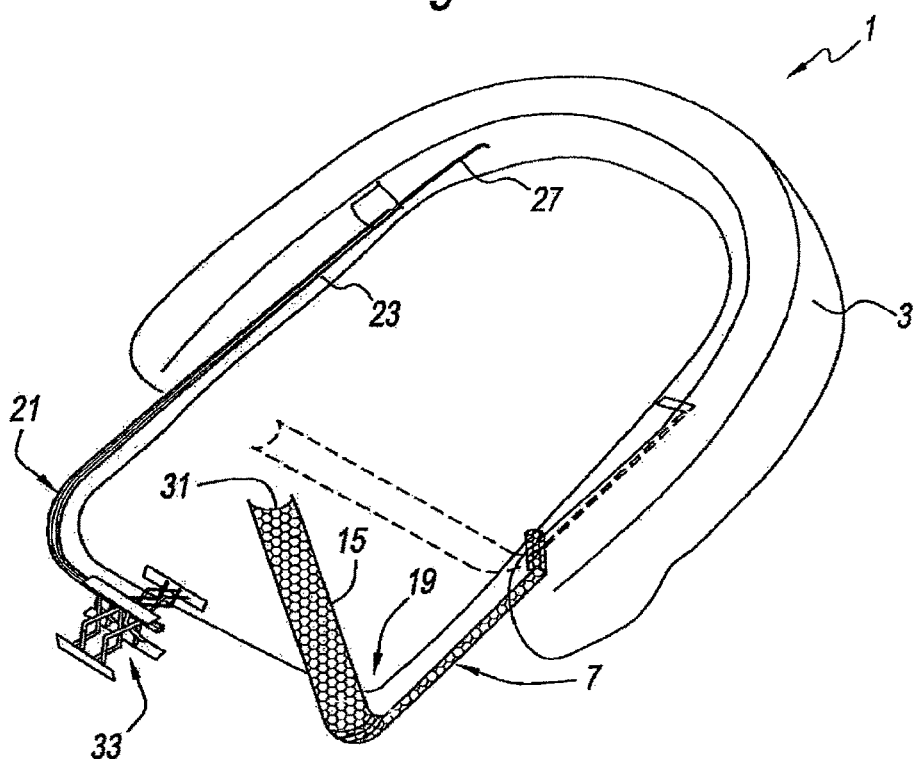
FIG. 4c is a front top perspective view of an oral appliance according to still another embodiment, wherein the soft palate wire mesh retainer has been directed upwards and the tongue retainer is a spring actuated expander that has been expanded axially by a push or pull method such that both retainers are in their active retention positions.

FIG. 4b is similar to FIG. 4a, except that soft palate retainer assembly 7 also includes memory wire 31, which avoids the need for mechanically moving assembly 7 into the active or inactive positions, as it is twisted into position by heat activation, such as a transition from room temperature to body temperature. FIG. 4c is similar to FIG. 4b, except that the bulb has been replaced with a spring actuated expander 33 or a small tube which can expand when positioned behind the soft palate via body activated temperature.

Figure 5A:
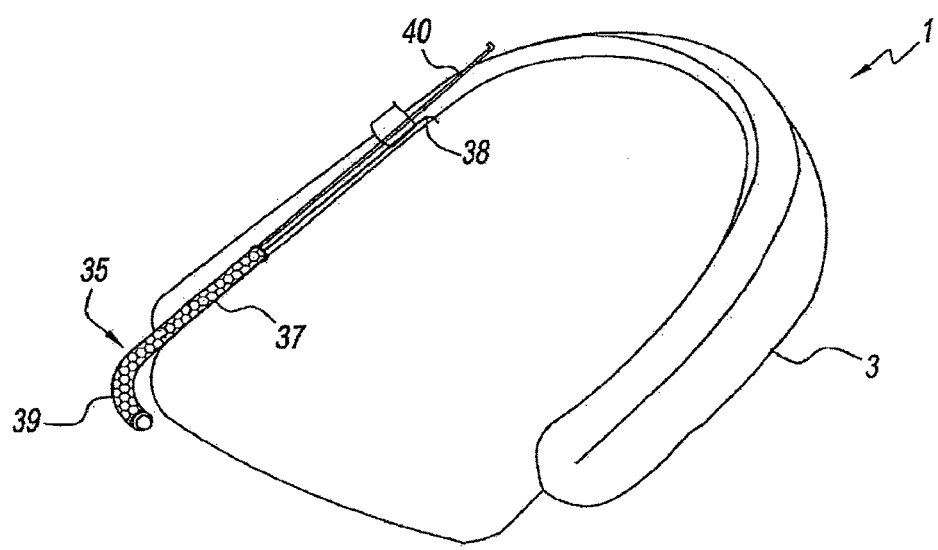
FIG. 5a is a front top perspective view of an oral appliance according to yet another embodiment of the present disclosure, wherein a tongue retainer is enclosed within a small tube housing.
Figure 5B:
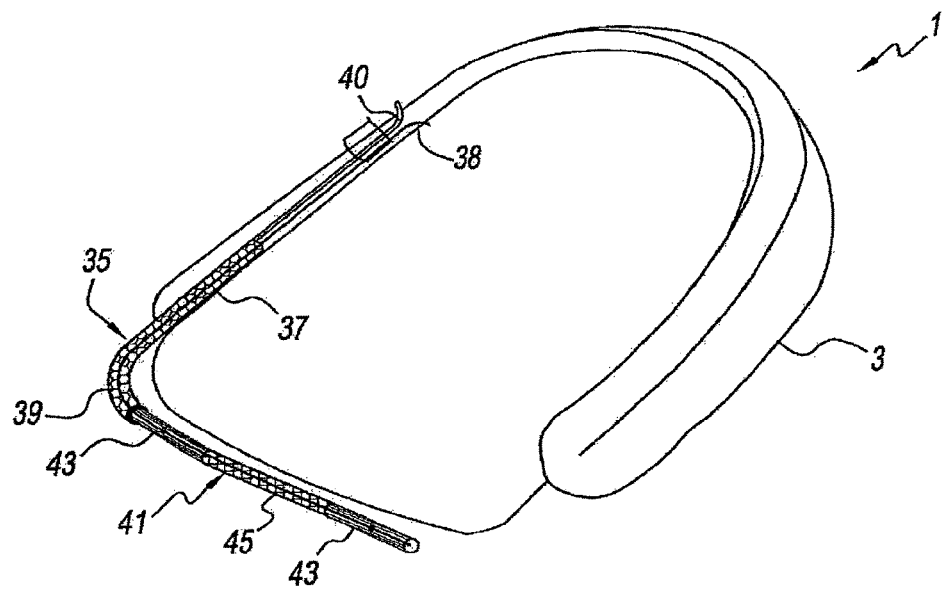
FIG. 5b is a front top perspective view of the oral appliance of FIG. 5a, wherein the tongue retainer has been exposed from the tube housing in a minimal non-expanded position.
Figure 6A:
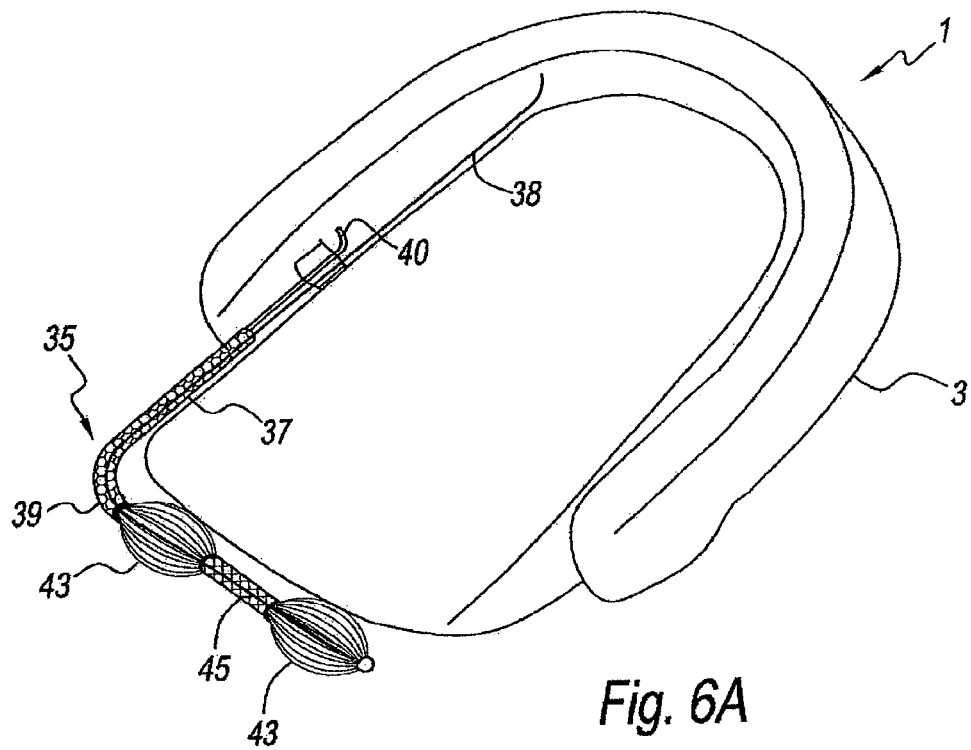
FIG. 6a is the oral appliance of FIG. 5b, wherein the tongue bulb retainer has been expanded via a pull method.

FIGS. 5a, 5b and 6a depict still yet another embodiment, wherein tongue retainer assembly 35 is disposed about one side of retainer 3. Assembly 35 comprises a tube 37 having an acute end portion 39, a pull rod or wire 38 and a push rod or wire 40, wherein tube 37 is configured to house expander 41. Expander 41 can have any shape and design, provided that it can provide support of the tongue (not shown) and provide a clinically efficacious air passage between the tongue and oropharynx and laryngopharynx regions. Preferably, expander 41 comprises a pair of expandable bulbs 43 disposed between a rigid intermediate portion 45. Expander 41 is preferably extracted from tube 37 via any mechanical or electromechanical device, including a push rod or wire 40. Once expander 41 is removed from tube 37, then pull wire or rod 38 can be pulled to expand bulbs 43, as shown in FIG. 6a.

Figure 6B:
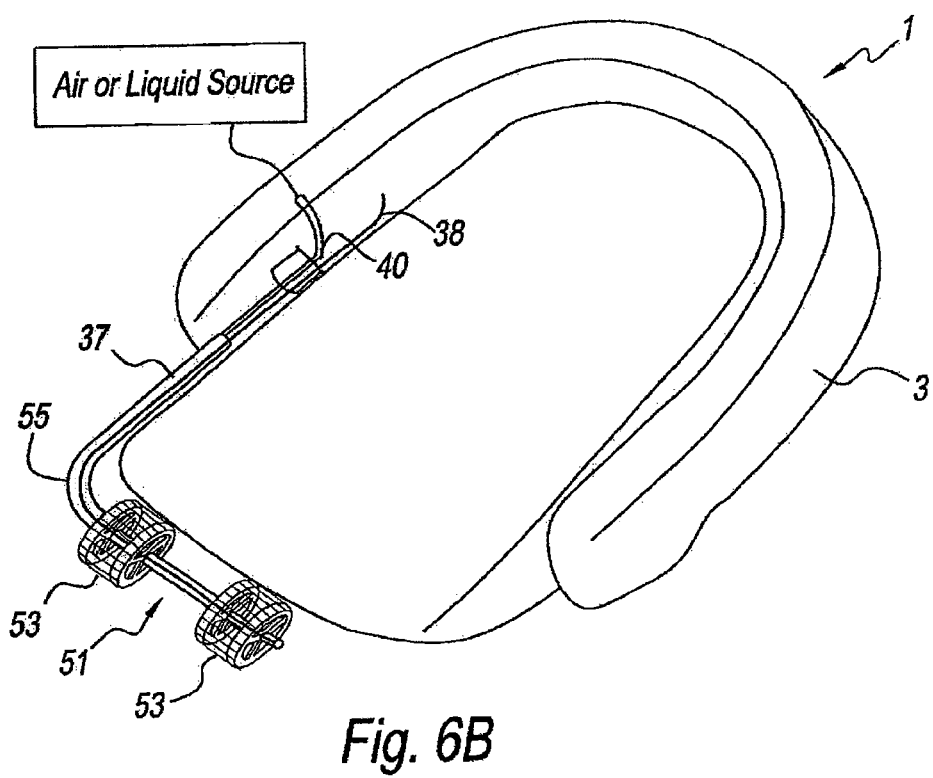
FIG. 6b is the oral appliance of FIG. 6a, wherein the bulbs in the tongue retainer has been replaced with inflatable rings.
Figure 6C:
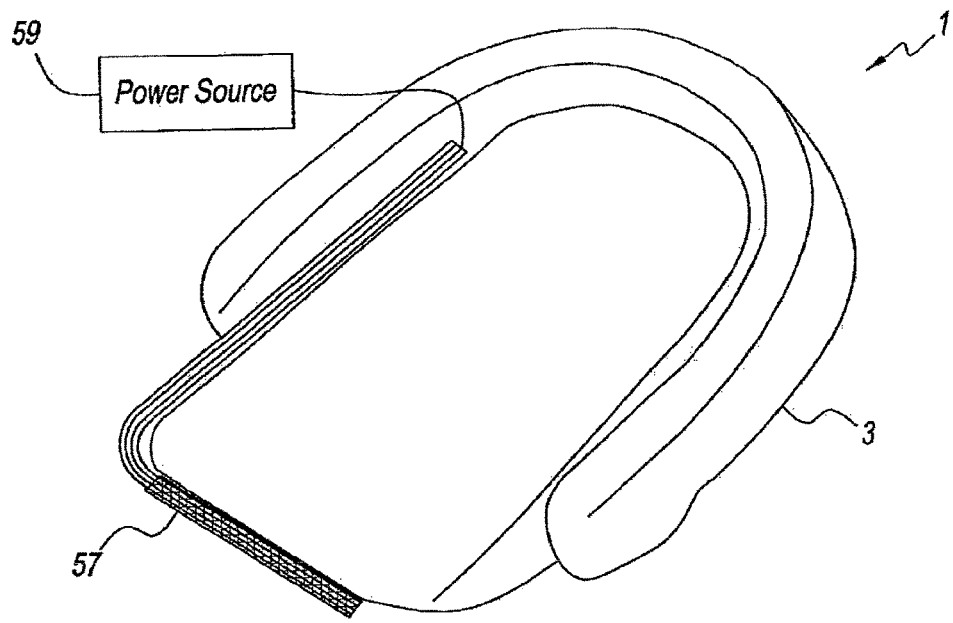
FIG. 6c is the oral appliance of FIG. 6a, wherein the bulbs in the tongue retainer has been replaced with an electronically activated metal wire.
Figure 6D:
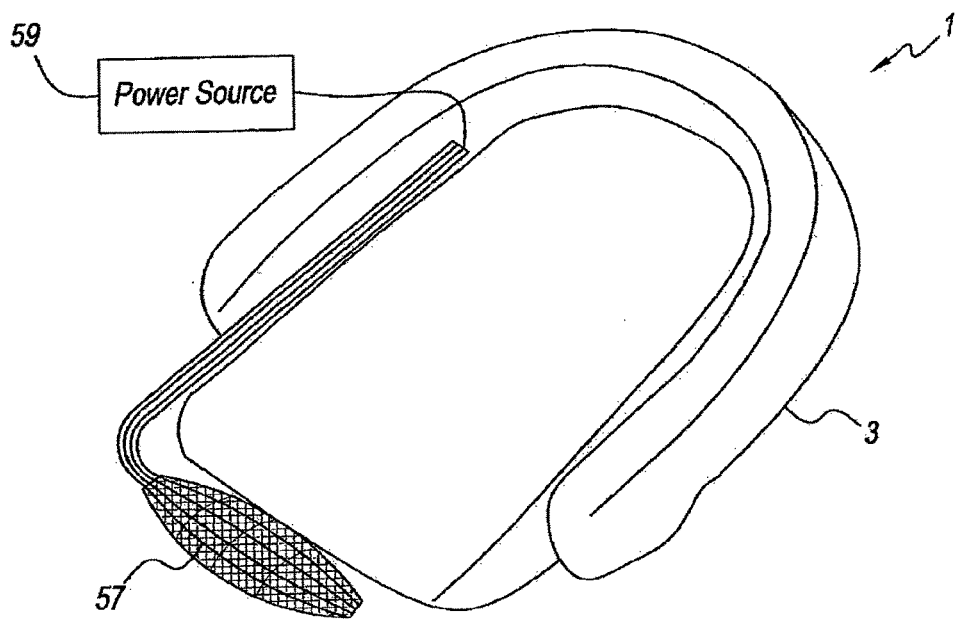
FIG. 6d is the oral appliance of FIG. 6c, wherein the metal wire is expanded into an oblong-shape by means of a power source being activated.
Figure 6E:
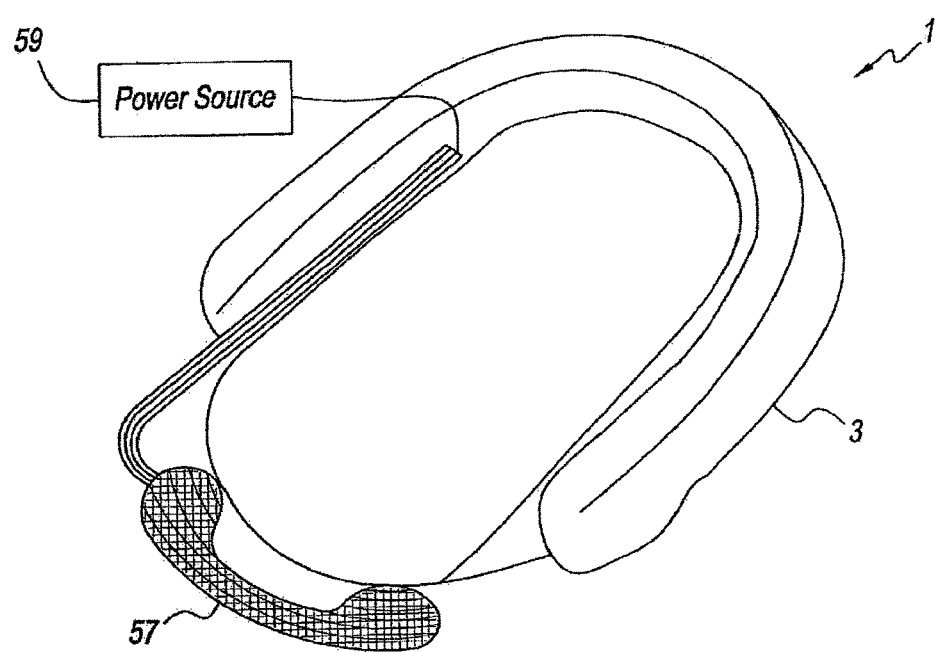
FIG. 6e is the oral appliance of FIG. 6c, wherein the metal wire expands into a head rest-shape, i.e. two large end portions disposed between a centrally disposed smaller portion, by means of a power source being activated.

FIG. 6b is an alternative embodiment of FIG. 6a, wherein expander 51 comprises at least one pair of inflatable spacers 53 radially disposed about tube 55. Alternatively, each spacer 53 can be a single spacer rather than a pair of spacers. Tubes 53 can be inflated via tube 40 by a gas, a liquid or a combination thereof. Preferably, spacers 53 are enclosed within a mesh to provide additional support and rigidity. During extraction from the mouth, the gas or liquid source is simply released through a small valve attached to the side of the retainer thereby causing spacer 53 to collapse allowing for ease of extraction. Spacer 53 can alternatively be comprised of very thin balloons, such as balloons surrounded by a plurality of non-connected segmented tubes. FIG. 6c is a further embodiment of FIG. 6a, wherein expander 57 is a metal wire connected to a power source 59, wherein the metal wire or shaped plastic expands as shown in FIGS. 6d and 6e when an electric current is supplied thereto via power source 59. Expander 57 is preferably surrounded by an insulation material (not shown) to avoid electricity and heat coming into contact with the patient. Additionally, such metal wire or shaped plastic can take any shape, such as flat in the middle with two oppositely disposed expanded portions. FIG. 6d takes on an oblong-shape and FIG. 6e takes on a head rest-shape, i.e. two large end portions disposed between a centrally disposed smaller portion.

Figure 7A:
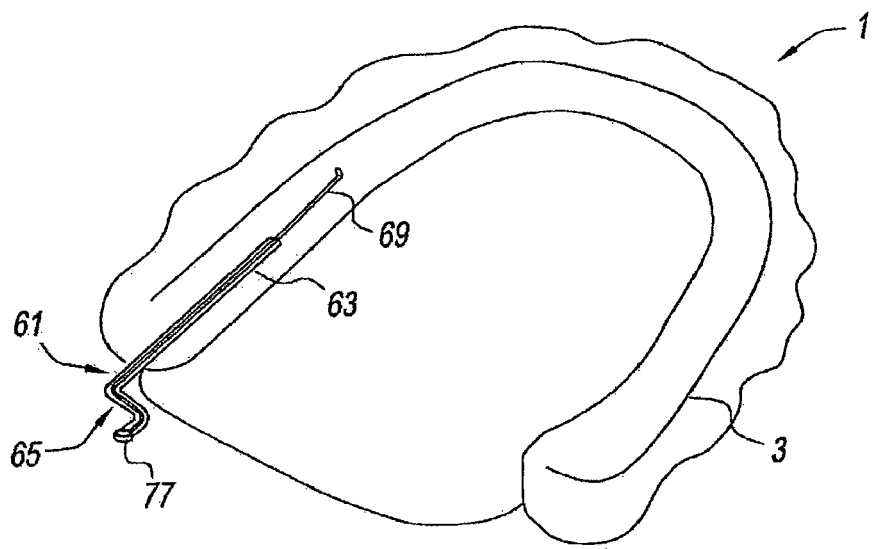
FIG. 7a is another embodiment according to the present disclosure depicting expandable cylinders in the closed position.

FIG. 7a depicts still yet another embodiment, wherein retainer 3 comprises a retainer assembly 61. Retainer assembly 61 comprises a support tube 63 having a serpentine shaped end portion 65. End portion 65 being connected to thin tube expander assembly 77. A push wire or rod 69 is disposed through support tube 63 for the purpose of expanding (FIG. 7b) or contracting (FIG. 7a) catheter like, thin flexible tube expander assembly 77, but firm enough to stay in place during usage.

Figure 7B:
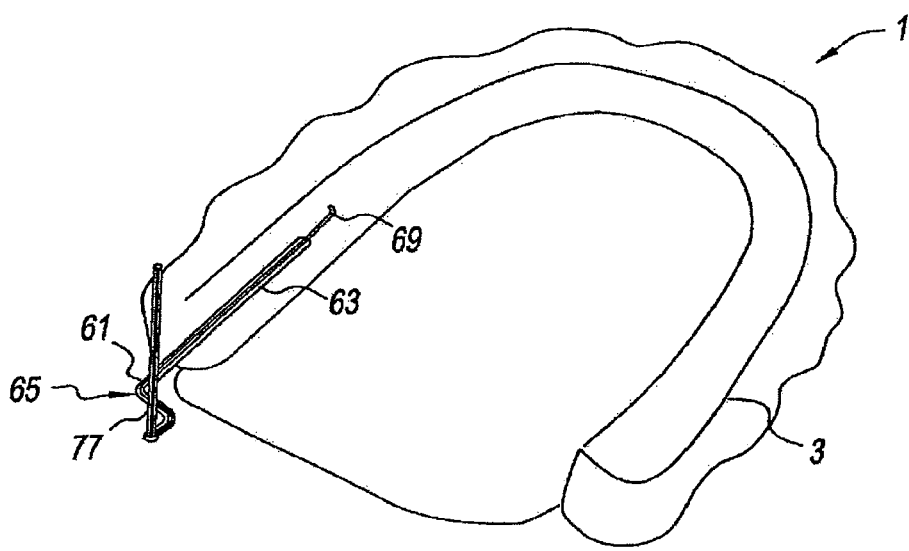
FIG. 7b is the oral appliance of FIG. 7a, wherein a thin flexible tube protrudes from the cylinder while in the expanded position, thereby providing support for the soft palate.
Figure 7C:
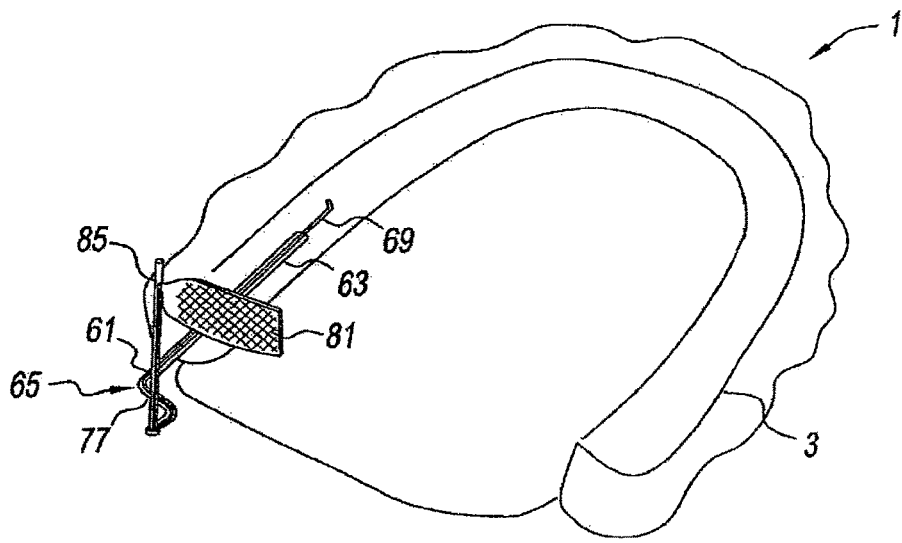
FIG. 7c is the oral appliance of FIG. 7b, wherein the upwardly projecting thin tube soft palate retainer includes a horizontally disposed mesh flag portion extending from the top portion of the thin tube.
Figure 7D:
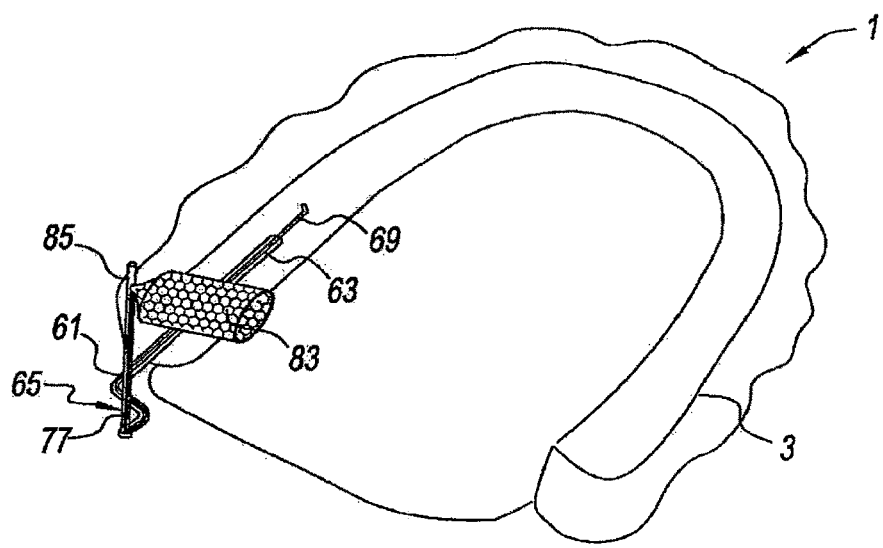
FIG. 7d is the oral appliance of FIG. 7b, wherein the upwardly projecting thin tube soft palate retainer includes a horizontally expanded mesh cylinder or stent extending from the top portion of the thin tube.

FIGS. 7c and 7d show alternative embodiments of FIGS. 7a and 7b, wherein upwardly disposed thin tube 77 has an expandable flag-type mesh 81 and stent or mesh support 83, respectively, perpendicularly protruding from an end portion 85 of thin tube 77, which can alternatively attach to a magnet disposed in a retainer connected to the upper or lower jaw (not shown) to keep soft palate open.

Figure 9:
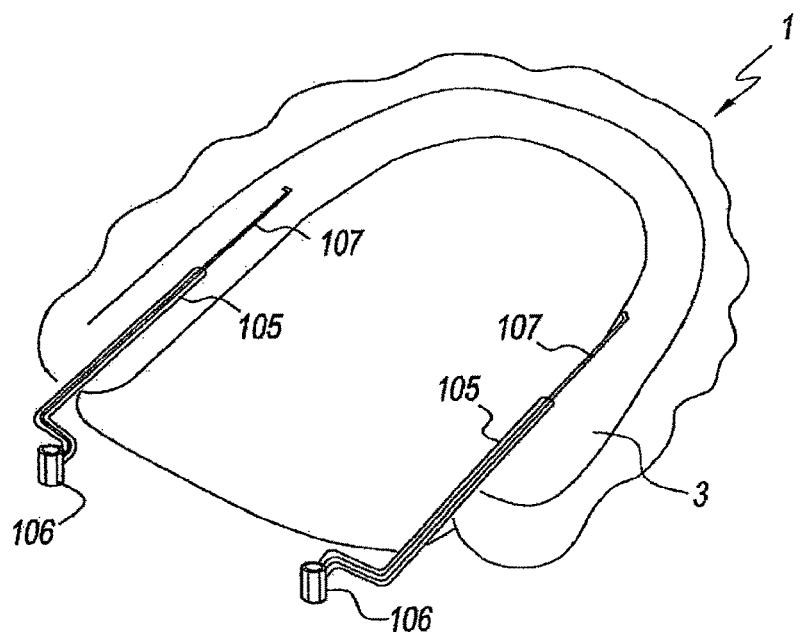
FIG. 9 is a front top perspective view of still yet another embodiment according to the present disclosure, wherein a pair of oppositely disposed thin round retainer tubes are disposed the soft palate and tongue.
Figure 9A:
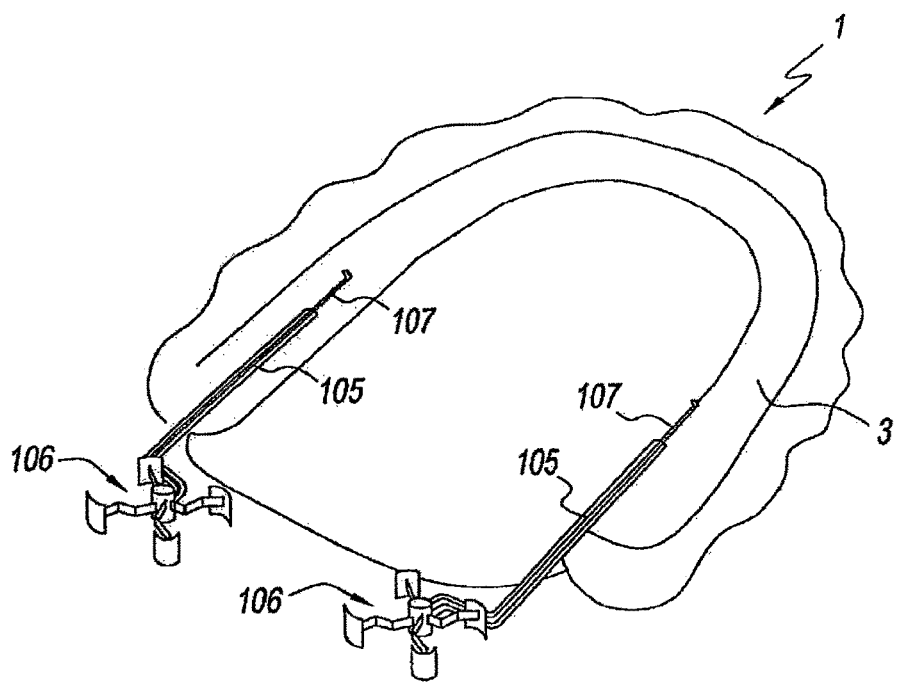
FIG. 9a is the oral appliance of FIG. 9, wherein the thin round retainer tubes are expanded in the radial direction.

FIGS. 9 and 9a depict still another embodiment according to the present disclosure, wherein a pair of oppositely disposed expandable thin round cylinders 106 are secured to retainer 3 via tubes 105 and expand by means of push rod 107 to provide an air passageway between the soft palate and/or tongue and the back of the throat (not shown).

In order to minimize a patient's gag reflex, another embodiment utilizes a shaped memory wire or plastic, which changes from a minimal shape to an expanded shape one in position behind the soft palate or base of tongue.

Optionally, a body temperature or otherwise heat-activated memory component, e.g., shape memory alloys and plastic memory alloys, could cause the desired expansions, such as by activating an expansion assembly. The activation can be achieved by the shape memory component contracting during a temperature change, and applying the resulting tension to a biasing member comprising a cam or lever expansion mechanism. When activated, such as by the contraction of a Nitinol wire, this cam or lever expansion mechanism exerts a force on a portion of the patient's airway. Alternatively or additionally, the tension or shape change of a shaped memory element can be used to cause volumetric compression of a biasing member, such as to remove the appliance from the patient's airway. In preparing the shape memory alloy or plastic for use in a patient, the shape memory alloy or plastic can have its temperature lowered to below body temperature prior to insertion into the patient by any know chilling device, such as a refrigerator, ice water bath, freeze spray, or any other chiller. Still other mean for expansion and maintaining the air passageway open, the present disclosure may involve the use of the following to cause expansion:

i) Electrically activated memory wires—which can apply significant force in tension to a cam or lever based expansion assembly. For, example, memory alloys, such as Nitinol wire, will shorten in length (with significant force) and assume different forms when heated, including resistive heating achieved through passage of electrical current through the wire. The thin strands of wire can lift thousands of times their own weight. Memory wire returns to its original shape and length when it cools. The direct linear motion of Muscle Wires made from memory wire offers a source of motion that is very similar to that of a human muscle, providing possibilities not available with motors or solenoids. Memory wire may be heated by any means, air temperature, hot water, body temperature or most commonly by running electric current through it. Although soft and pliable like a nylon thread under normal conditions, memory wire can become stiff like a piano wire and contracts. As the wire is cooled (e.g. if the passage of a current is stopped), the wire will soften and extend to its original length. Such a quick return to its flexible and supple form will allow for an easy retraction of any device behind the soft palate or base of tongue. In this application a wire or wires in its 'deformed' and supple state can have a small cross section when placed in the retainer tube. Once in place behind the tongue or soft palate, the wires can be triggered by electrically generated heat or heat from the body to return to its original memory shape. Shape memory alloy (SMA) devices can open and constrict and push apart and can be used to provide an active stent for the airway. When a shape memory alloy is heated through its transformation temperature, it recovers its previous shape with great force, undergoing a phase transformation in its crystal structure.

ii) Piezoelectric devices can replace mechanical expanders, as a piezoelectric device can produce a small displacement with a capability for high force when electricity is applied. Such a device could cause an expansion device to expand behind the base of tongue as well as to quickly contract the moment the electricity were turned off—so as to allow for easy removal. Electrostrictive materials are somewhat similar to piezoelectric materials and change shape when electrical voltage is applied. Dielectric elastomers (Des) are smart materials that have the capability of producing large strains and changes in shapes from the application of an electric field. An electric field can expand a DEA membrane iii) smart fluids—magneto-rheological fluids (MRFs) and electro-rheological fluids (ERFs). MRFs solidify in the presence of a magnetic field and re-liquefy when that force is removed. With ERFs contained within, a biasing member such as a stent or balloon could stiffen through the application of an electrical field and soften when that electric field is removed.

iv) Shape-memory polymers—materials that transform themselves into a pre-determined shape when activated—these polymers require direct triggering by light or direct heat or by changes in pH. Rigid space structures can be transformed from their initially flexible state. There are also shape-memory polymers that are triggered remotely by a magnetic field, making it possible to activate them once placed behind the soft palate or the base of tongue. Magnetostriction is the material property that causes a material to change its length and form when subjected to an electromagnetic field.

Each of the appliances of the present invention may include or otherwise be attachable to one or more supplies of power, such as a battery, to cause an electrically activated device to change shape or apply a force, to cause a biasing member to expand and/or contract, as has been described in detail hereabove.

A second aspect of the present disclosure generally pertains to a unique and novel medical appliance and method for directly applying a force to a patient's soft palate and/or tongue for the purpose of minimize the discomfort and allow for swallowing while treating the patient for one or more sleep disorders such as sleep apnea or severe snoring. A nasal tube or wire of the present disclosure enters the patient through the nasal passageway in a minimally invasive way and thereafter expands only in the necessary areas to open the airway behind the soft palate and/or tongue. The appliance can be custom manufactured and/or adjusted to meet the particular needs of each patient.

Figure 10:
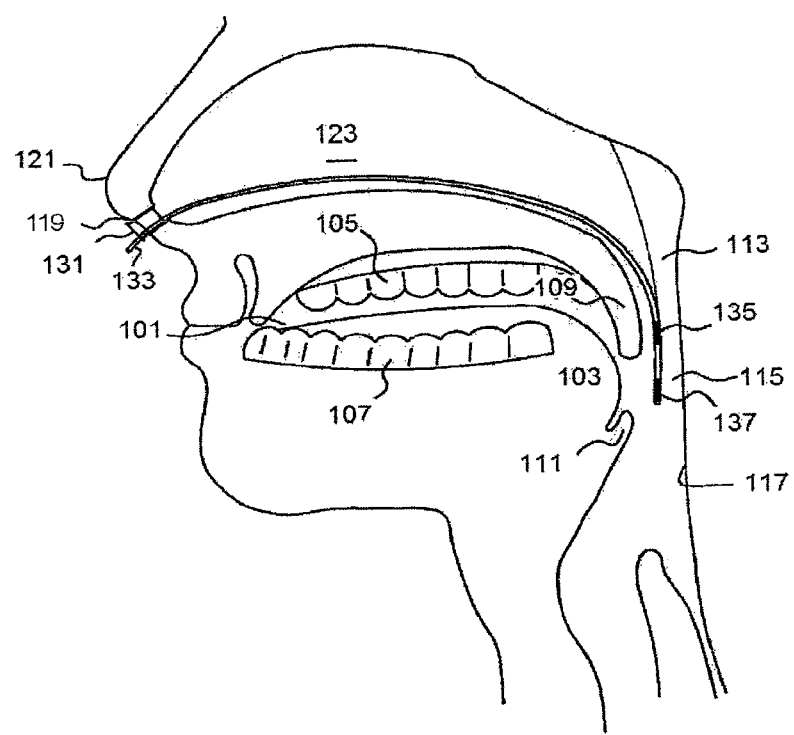
FIG. 10 is a cross-sectional view of a patient's soft palate, oral cavity and pharynx with a nasal appliance according to the present disclosure disposed therein in a collapsed position.
Figure 11:
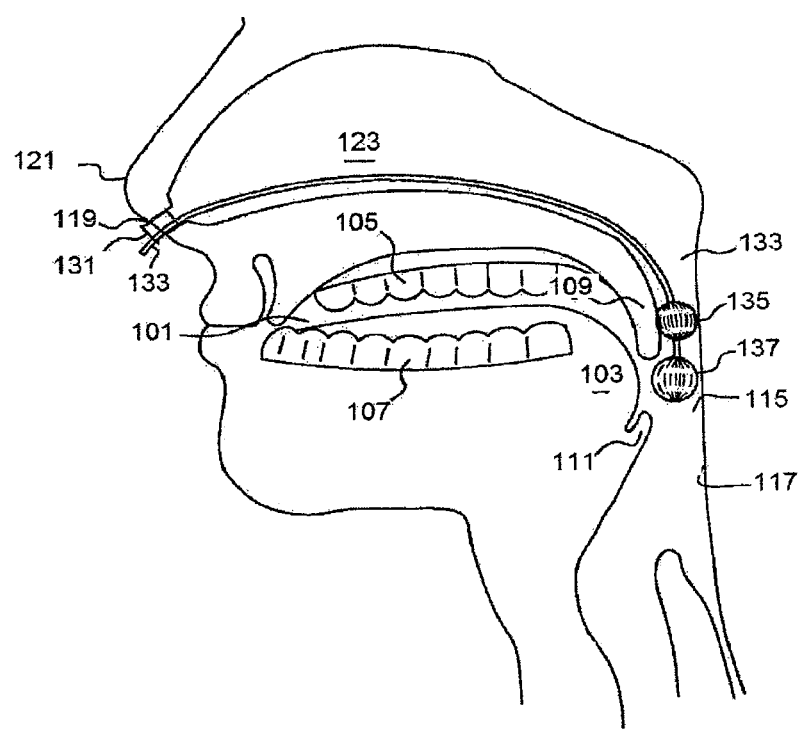
FIG. 11 is a view of FIG. 10, wherein the nasal appliance is in an expanded position with a pair of balloons according to the present disclosure.
Figure 12A:
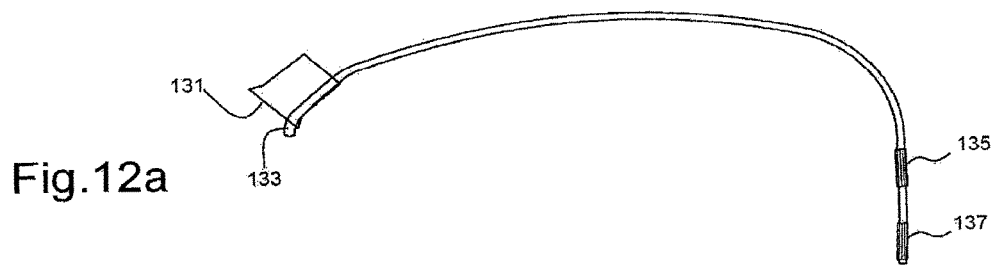
FIG. 12a is the nasal tube according to FIG. 10 in the collapsed position.
Figure 12B:
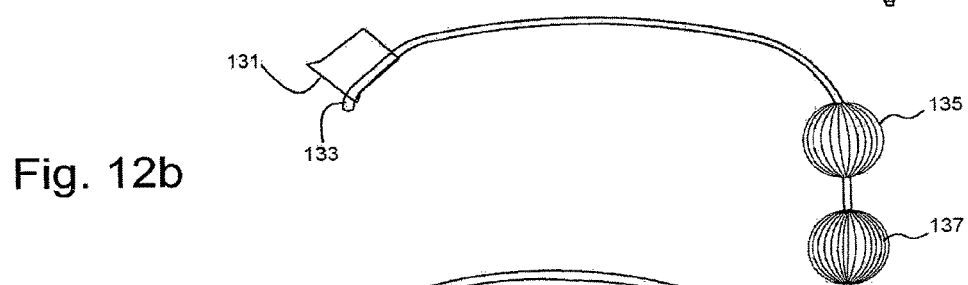
FIG. 12b is the nasal tube according to FIG. 11 in the expanded position.

FIG. 10 shows the patient with a nose cone 131 disposed within nasal valve 119 so as to allow air and nasal tube 133 to pass therethrough into nasal passageway 123, nasopharynx region 113, oropharynx region 115 and/or laryngopharynx region 117. Nasal tube 133 has a pair of expanders 135,137, shown in the collapsed position. FIG. 11 shows expanders 135,137 in the expanded position. Expanders 135,137 are preferably formed of a plurality of thin tubular balloons encased in a air permeable mesh cover, wherein the plurality of balloons are preferably in an "arch" shaped configuration and encased and attached to the mesh cover, thereby preventing their collapse when under pressure. The collapsed expanders 135, 137 can be seen in FIG. 12a and the expanders can be seen in FIG. 12b in their expanded position.

Figure 11A:
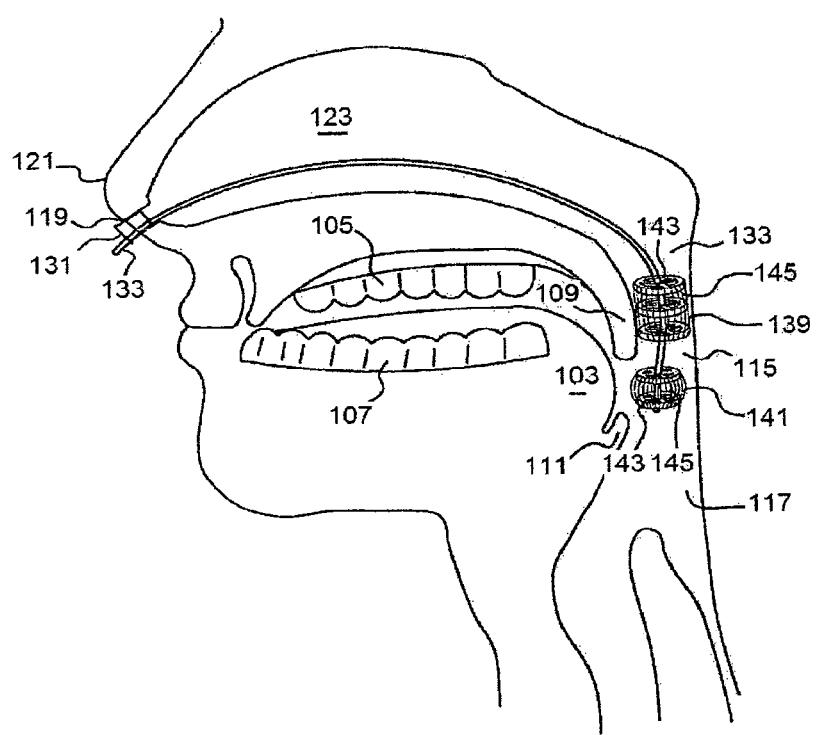
FIG. 11a is an alternative embodiment, wherein the pair of balloons has been replaced with a plurality of radially expandable disc-shaped expanders.
Figure 13A:
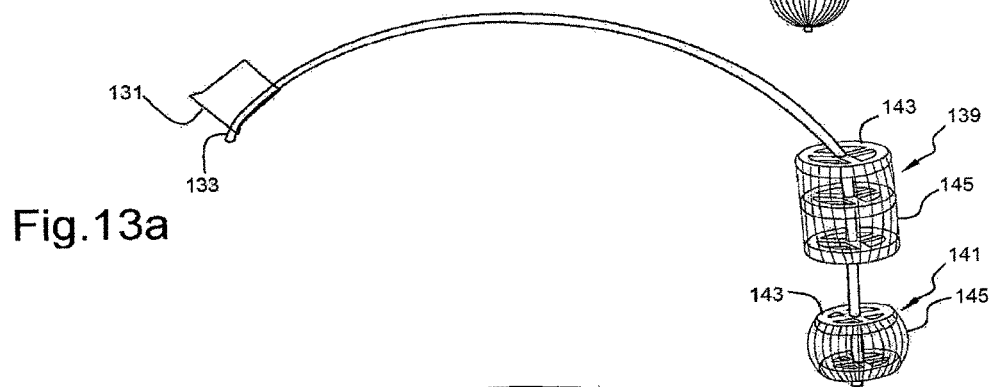
FIG. 13a is the nasal tube according to FIG. 11a in the expanded position.

FIG. 11a is another embodiment wherein a pair of expanders 139,141 are configured such that they are formed by a plurality of radially disposed inflatable disc-shaped expanders 143, shown in the expanded position. Expander 139 shows three disc-shaped expanders 143 encased in a mesh 145, whereas expander 141 includes two disc-shaped expanders 143 encased in a mesh 145, although any number of disc-shaped expanders 143 can be used to form expander 139 or 141. FIG. 13a shows nasal tube 133 with expanders 139, 141, each having a plurality of radially disposed inflatable disc-shaped expanders 143 encased in mesh 145. In a particular embodiment, expanders 143 have provide different radial strength, such as with the most superior expander offering more radial strength than the most inferior, such as to accommodate patient swallowing when expanders 143 are placed behind the soft palate. In another particular embodiment, two or more expanders are separated at a central connection point (as shown), but attached to each other at their outer diameter (not shown but preferably attached at one or more points or along their entire circumference, forming a triangular cross-section).

Figure 11B:
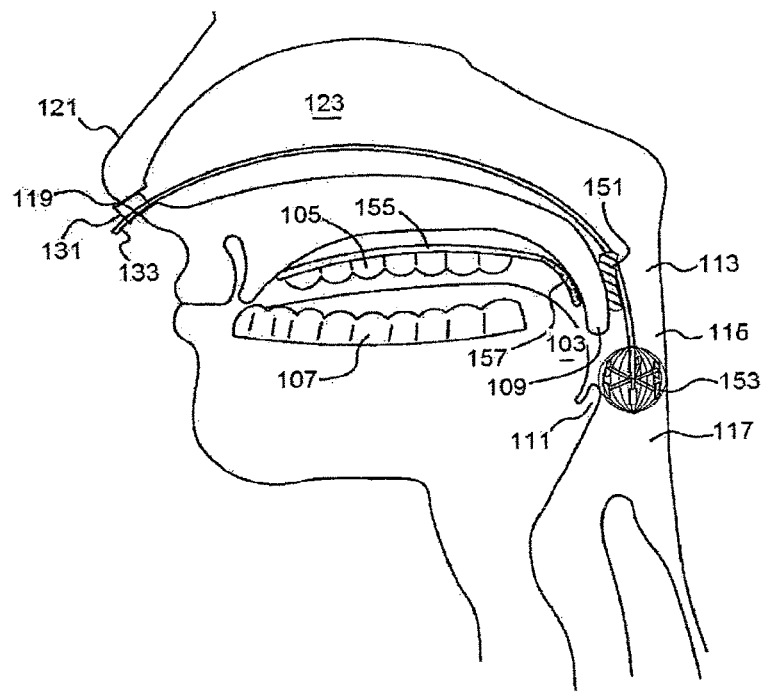
FIG. 11b is another embodiment, wherein the nasal tube has a metal or magnet disposed about the soft palate and a mesh encased expander disposed about the tongue.

FIG. 11b is yet another embodiment wherein nasal tube has a metal or magnetic component 151 disposed about the nasophrynx region 113 and contact with soft palate 109, and an expander 153 disposed between the oropharynx region 115 and laryngopharynx region 117 such that it is in contact with tongue 103. A retainer 155 is disposed about upper jaw 105 and comprises a magnetic or metal portion 157 disposed about one end portion thereof such that it is substantially opposite associated metal or magnet 151, wherein soft palate 109 is disposed therebetween. This configuration allows for the magnetic portion 157 to pull soft palate 109 and metal or magnet 151 away from the back wall of the nasophrynx region 113, thereby providing an open air passageway therein. In an alternative embodiment, metal or magnet portion 157 and/or metal or magnet 151 is an electromagnet, such as an adjustable force electromagnet attached to a battery, not shown but integral to a component of the appliance. Magnetic force adjustment can be used to improve flow of air (increase in force) or improve patient comfort (decrease in force).

Figure 11C:
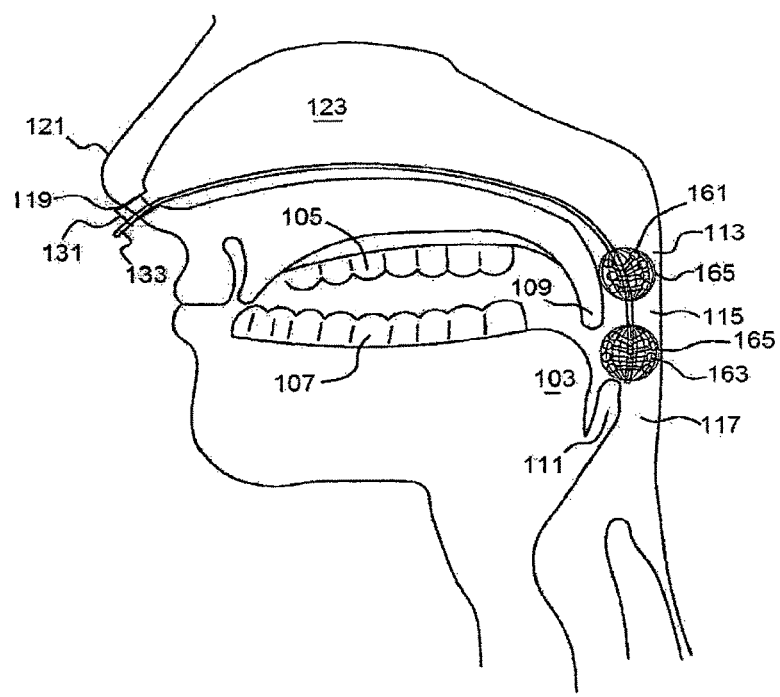
FIG. 11c is still another embodiment, wherein a pair of mesh encased multiple balloon expanders are disposed opposite the soft palate and tongue, respectively.
Figure 13B:
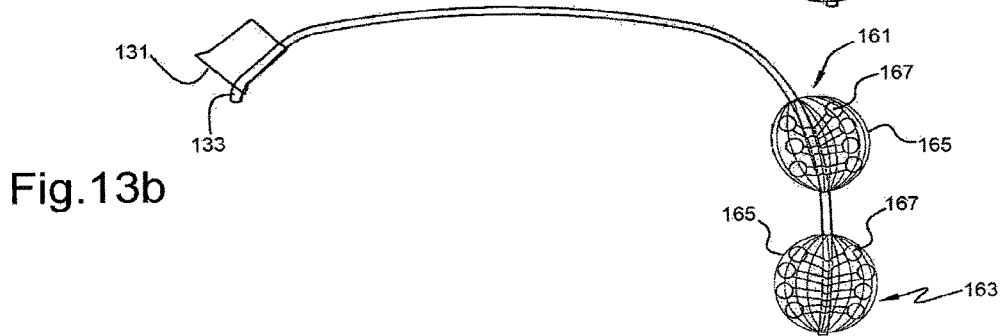
FIG. 13b is the nasal tube according to FIG. 11c in the expanded position.

FIG. 11c is another embodiment wherein nasal tube 133 comprises a pair of expanders 161, 163 formed of a plurality of balloons encased in a mesh 165. FIG. 13b shows balloons 167 encased in mesh 165 for both expanders 161,163.

Figures 14A, 14B:
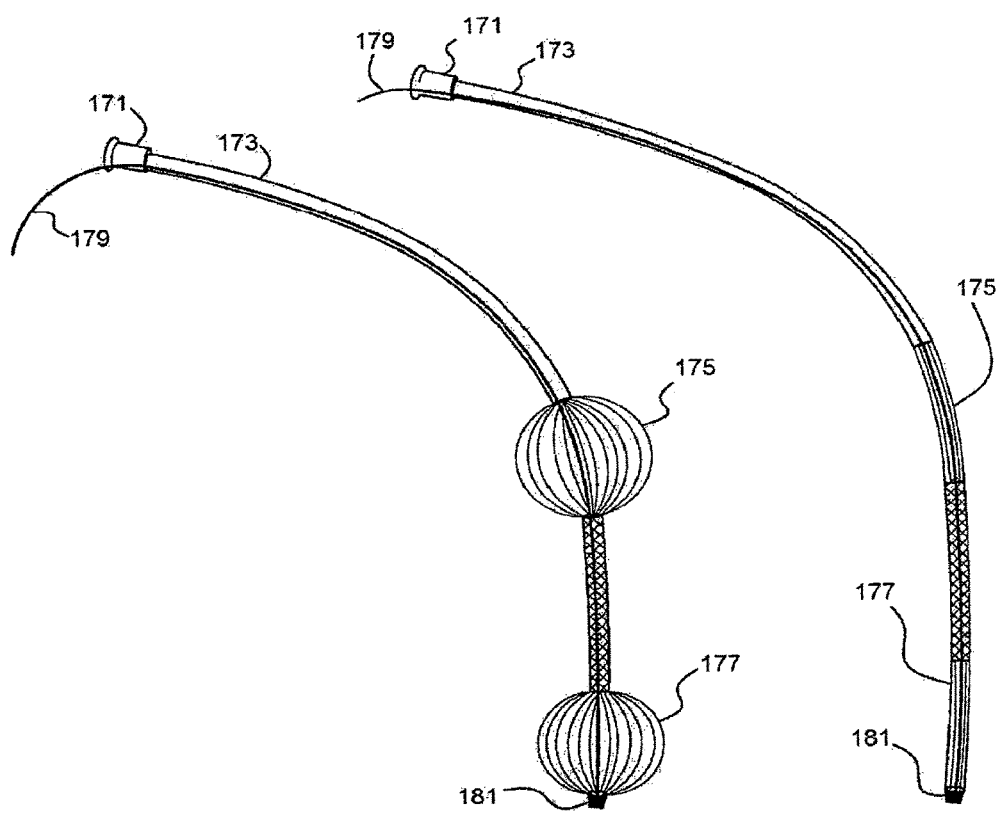
FIG. 14a is yet another embodiment of a nasal tube according to the present disclosure having a pair of expander which can be actuated via a pull mechanism.
FIG. 14b shows the expanders of FIG. 14a in the expanded position.

FIGS. 14a and 14b depict still another embodiment according to the present disclosure, wherein a nose cone 171 is connected to a nasal tube 173 having a plurality of expanders 175, 177, such that a pull wire 179 secured about one end of nasal tube 171 by a fastener 181. FIG. 14a shows expanders 175,177 in the collapsed position, whereas FIG. 14b shows expanders 175,177 in the expanded position wherein wire 179 has been pulled such that fastener 181 moves towards nose cone 171, thereby expanding expanders 175,177.

Figures 15A, 15B:
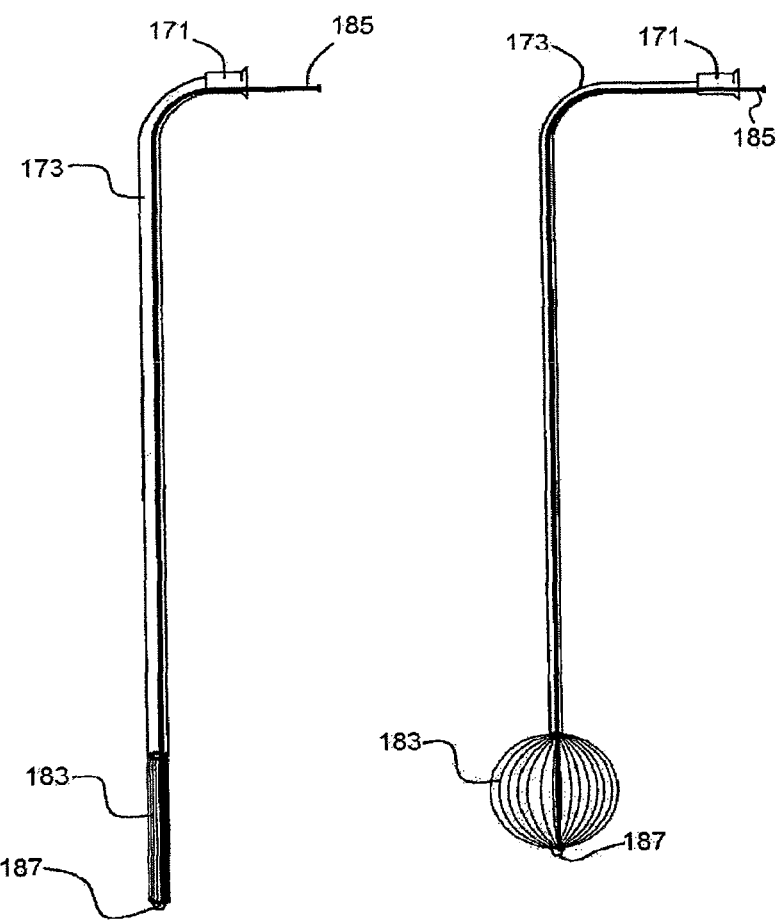
FIG. 15a is still another embodiment of a nasal tube according to the present disclosure having an expander which can be actuated via a push mechanism.
FIG. 15b shows the expander of FIG. 15a in the expanded position.

FIGS. 15a and 15b depict a nose cone 171, nasal tube 173, expander 183 and push wire 185. Similar to FIGS. 14a and 14b, push wire 185 traverses the entire length of tube 173 and is secured at one end via fastener 187. FIG. 15a shows expander 183 in the collapsed position, which is the preferred position when being inserted through the nasal passageway, not shown. Once in position, expander 183 can be expanded by means of pushing wire 185 toward fastener 187.

In order to minimize a patient's discomfort, another embodiment utilizes a shaped memory wire or plastic, which changes from a minimal shape to an expanded shape once in position behind the soft palate or base of tongue.

The amount of stenting or other applied force required is variable depending upon the needs of the patient. As such, the device of the present disclosure can be adjusted to meet such needs. In one embodiment, an adjustable electromagnet is used to apply force to the patient's soft palate and/or base of tongue.

Optionally, a body temperature, heat-activated memory wire, e.g., shape memory alloys and plastic memory materials, could cause the desired expansions, such as by applying tension to a lever or cam based expanding assembly. Still other mean for expansion and maintaining the air passageway open, the present disclosure may involve the use of the numerous electrically expanding or contracting assemblies described hereabove.

According to another aspect of the present disclosure, a unique and novel medical appliance and method are disclosed for directly stenting or otherwise applying a force to a soft palate and/or tongue of a patient for the purpose of minimizing the discomfort and to allow for swallowing while treating the patient for sleep apnea. The orally inserted appliance of the present disclosure enters the patient through the oral cavity in a minimally invasive way. The appliance is placed on the tongue like a tongue depressor with the end lip preferably positioned just behind the soft palate and to one side of the uvula. Thereafter the appliance is activated by pushing a plunger toward an expander, such that the expander is emitted from a hollow tube of the appliance. After the expander has extended behind the soft palate and tongue, it expands such that it opens or maintains the opening of the air passageway disposed behind the soft palate and/or tongue. Preferably, the expander is retained in the expanded position behind the soft palate and/or tongue by means of a retainer device and wire connected to the upper jaw of the patient.

Figure 16:
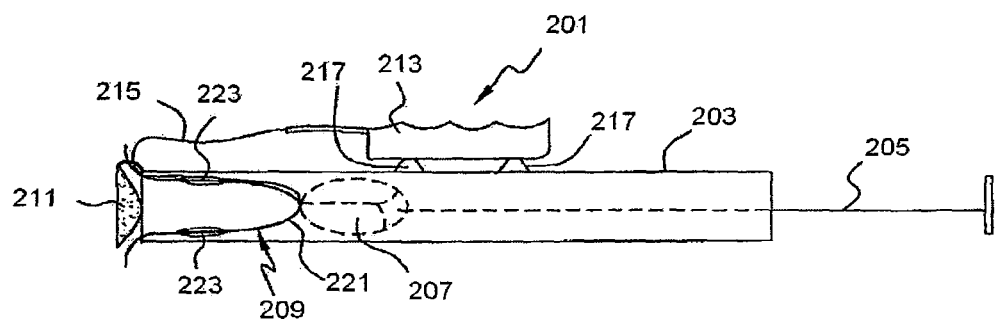
FIG. 16 is a right side planar view of an orally inserted appliance comprising an insertion applicator and associated airway expander according to one embodiment according to the present disclosure, wherein the plunger is in the retracted position.
Figure 17:
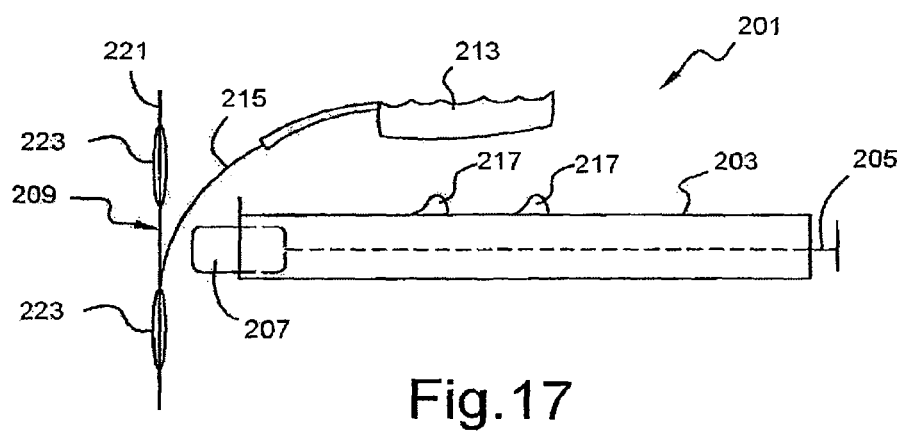
FIG. 17 is a right side planar view of the orally inserted appliance according to FIG. 16, wherein the plunger is in the expanded position such that the airway expander mechanism is dislodged from the hollow tube of the insertion applicator.
Figure 18:
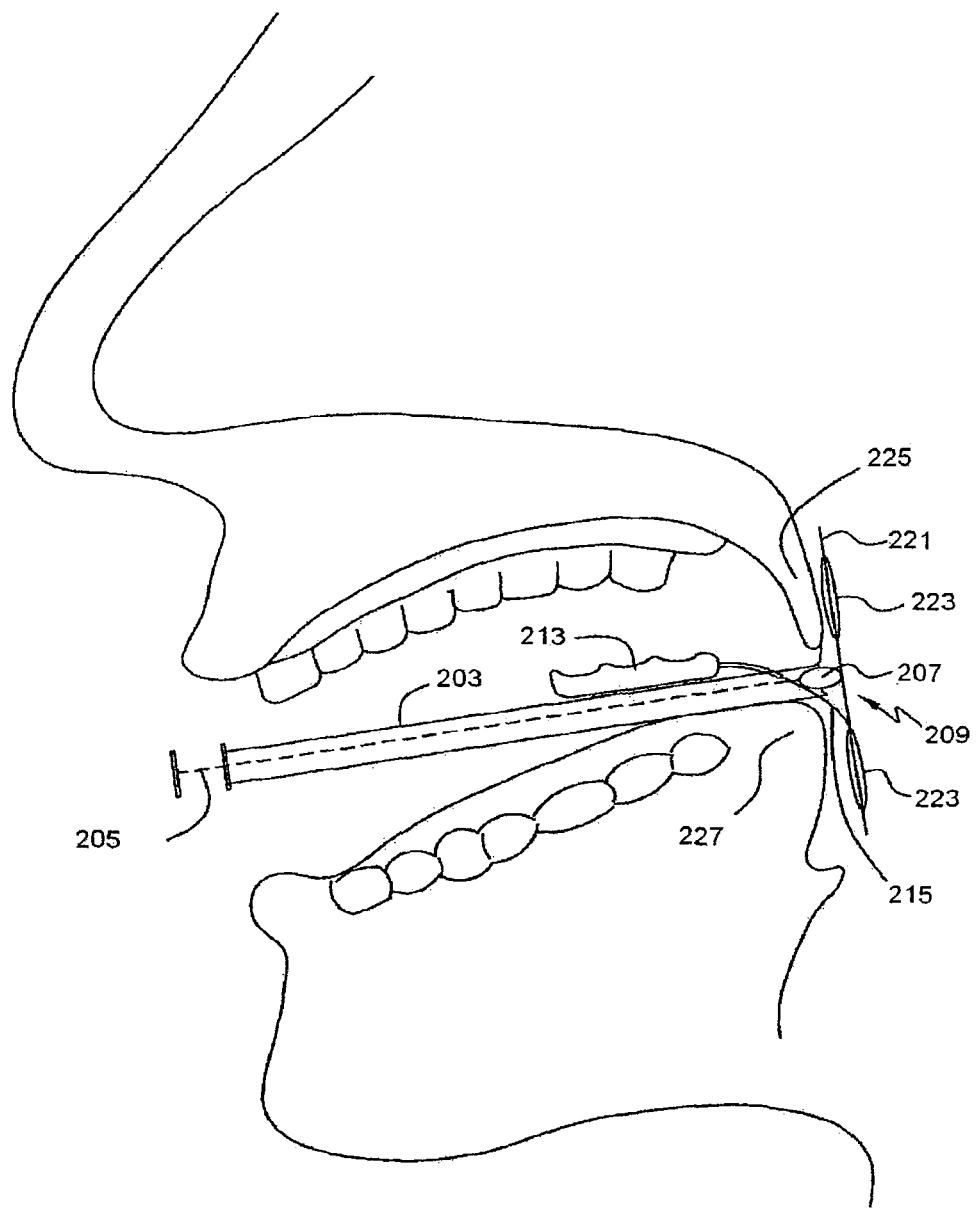
FIG. 18 is a right side view of the appliance of FIGS. 16 and 17, wherein the airway expander has been dislodged from the insertion applicator and positioned between and behind both a patient's soft palate and tongue according to the present disclosure.
Figure 19:
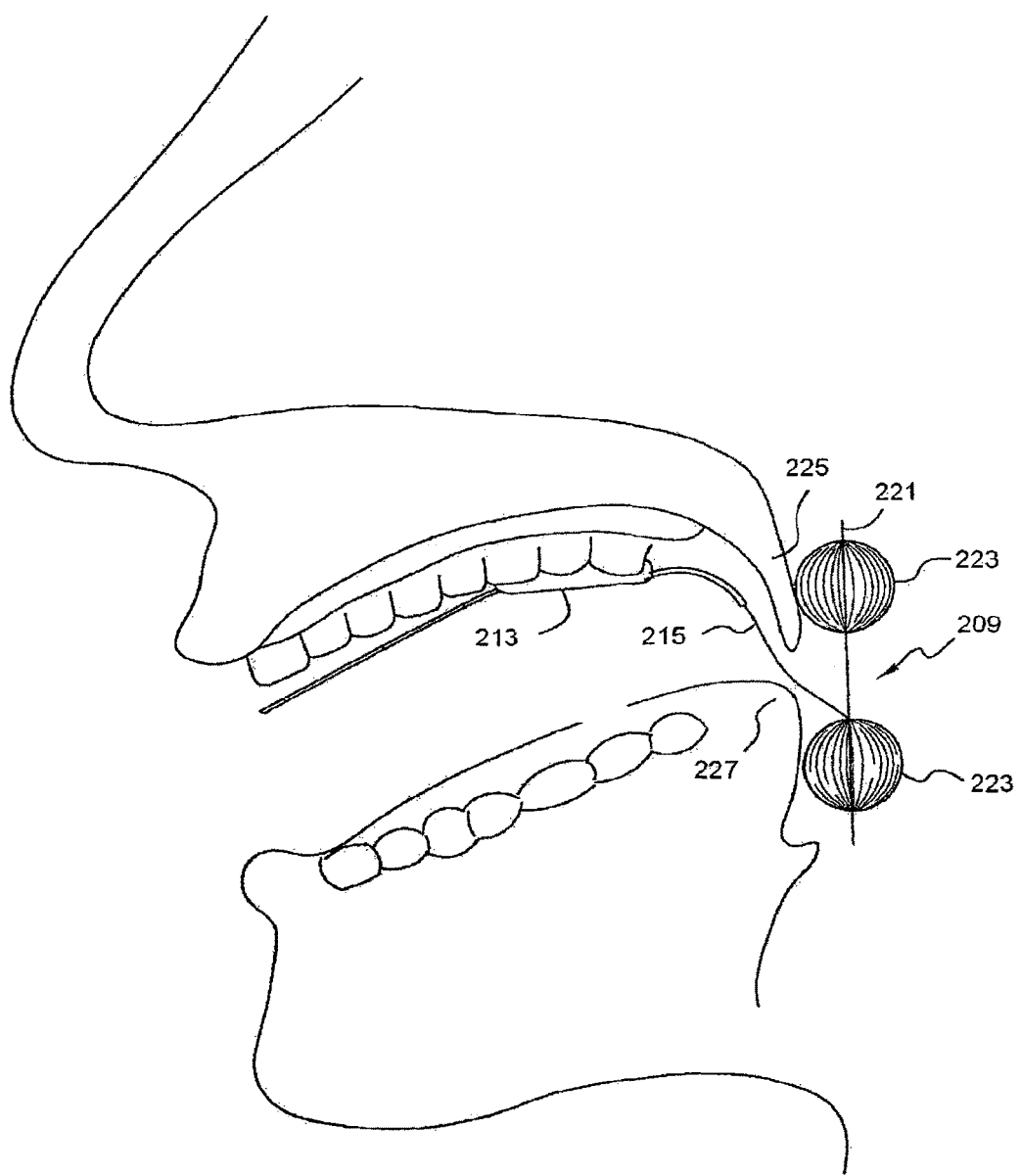
FIG. 19 is a right side view of the airway expander of FIG. 18, which has been expanded to allow for air to flow through behind the soft palate and tongue according to the present disclosure.
Figure 20:
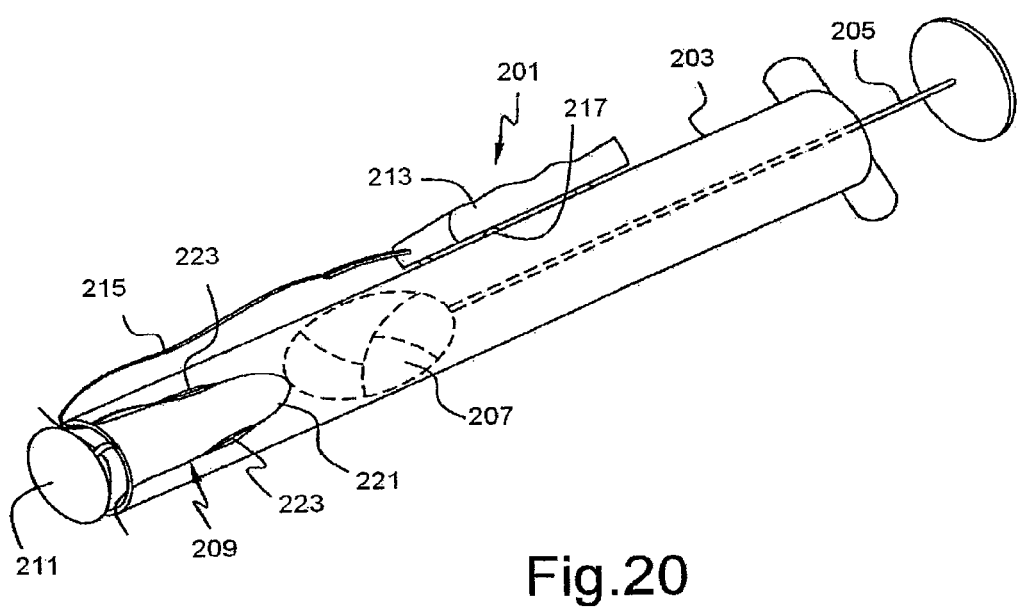
FIG. 20 is a front right side perspective view of the orally inserted appliance of FIG. 16, wherein the expanding it disposed within the hollow tube of the insertion applicator according to the present disclosure.

FIGS. 16 and 20 depict an orally inserted appliance 201 comprising a hollow narrow carrier tube 203, a plunger 205, and a plunger head portion 207. A bent expander 209 is disposed in contact with plunger head portion 207, and a cap 211 is movably secured to an end portion of plunger 205. Retainer 213 is connected by wire 215 to expander 209, and carrier tube mounts 217 are disposed about an exterior surface of tube 203 for mounting retainer 213 to tube 203. FIG. 17 depicts plunger head portion 207 having pushed expander 209 out of tube 203 with cap 211 being pushed aside. Expander 209 comprises a collapsible wire or tube 221 having at least one expandable biasing member such as a balloon or mesh ball. As shown in FIGS. 18 and 19, cylinder 223 is disposed such that in the expanded state, balls 223 maintain an opening in the air passageway behind soft palate 225 and the base of tongue 227.

Figure 21:
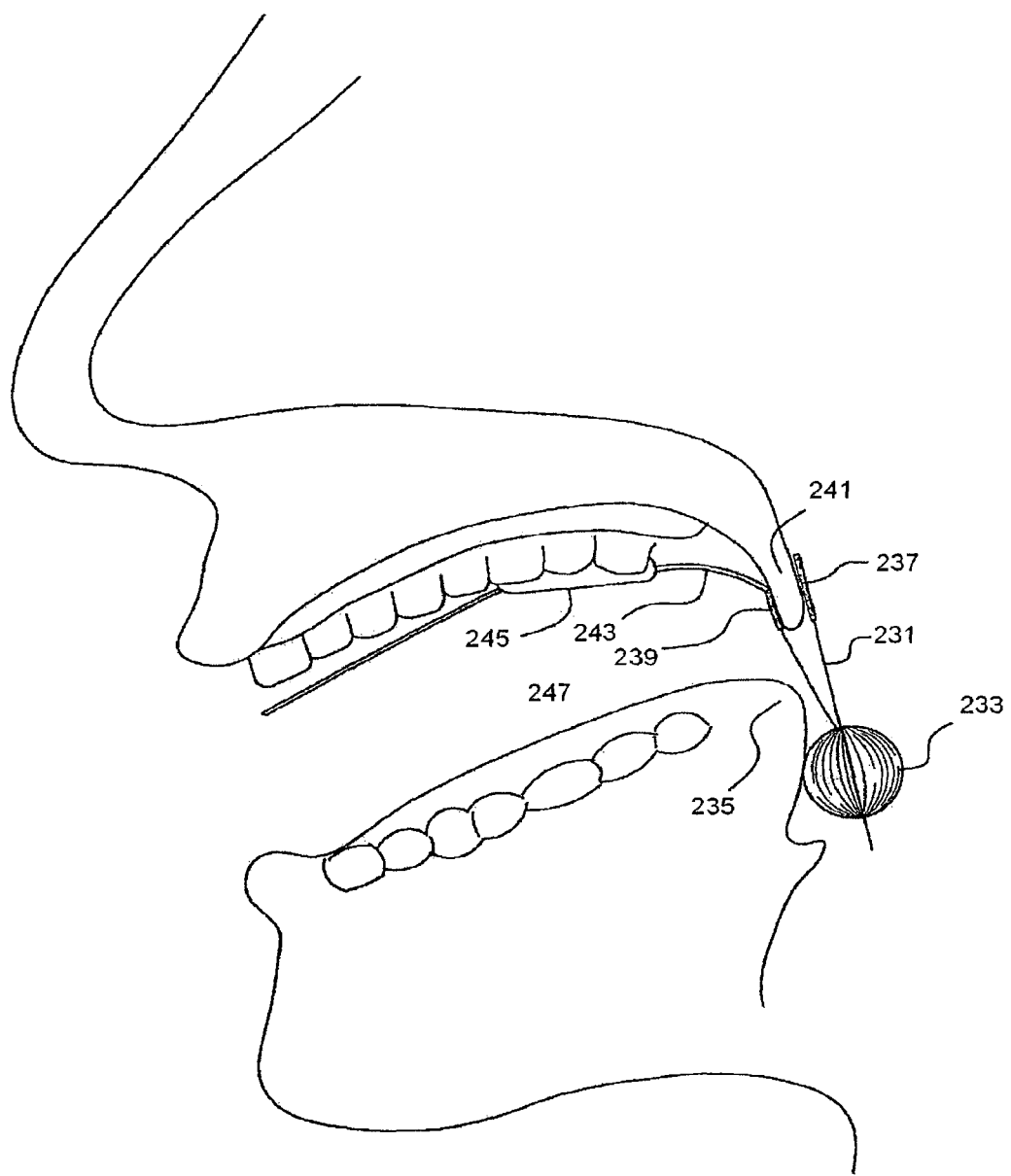
FIG. 21 is another embodiment according to the present disclosure, wherein the expander device includes a magnetic member capable of magnetically stenting open the air passageway behind soft palate and mechanically or by other means, keeping open the air passageway behind the tongue.

FIG. 21 shows another embodiment according to the present disclosure wherein collapsible wire or tube 231 has an expandable ball 233 disposed at one end thereof to maintain an airway behind the base of tongue 235 and a pair of magnets 237, 239 disposed about soft palate 241. Magnet 239 being connected to both tube 231 and retainer wire 243 such that the distance from retainer 245 and magnet 239 is maintained at a constant by retainer wire 243. Magnet 239 causes magnet 237 disposed on a side of soft palate 204 opposite thereto to ensure that soft palate 241 is pulled toward the oral cavity 247, thereby maintaining an air passageway behind soft palate 241.

In operation, a patient will insert the oral appliance into their oral cavity, similar to the insertion of a tongue depressor, with the end lip of the appliance preferably just behind the soft palate on one side of the uvula. The patient will depress the plunger such that the expander is expelled from the plunger device and expanded behind the soft palate and/or tongue. As the plunger is moved toward the back of the oral cavity, a triangular-shaped end cap on the plunger tube is opened by the force applied by the plunger, such that the cap is opened via a hinge or the like. As the expander is positioned behind the soft palate and tongue, the retainer is dislodged from the outer surface of the plunger and secured to the upper jaw of the patient, thereby ensuring that the expander remains in position in the patient's throat as the expander is attached to the inside edge of the retainer. The expander can be attached to an air tube to allow for air to be used to expand the expander balls, although other means of expanding the expander balls known to one of ordinary skill in the art are also contemplated herein.

For example, a tiny air tube can be attached to the middle of the tube expander tube and routed back through the retainer, which then is designed to receive an air tube from an outside air source.

As an alternative to the expander balls, the present disclosure also contemplates expanding the biasing members of the present invention using other technologies to expand the balls, such as expandable wire mesh balls, or other shaped materials configured to stent or otherwise apply a force to keep the airways open such as, temperature sensitive or electrically activated memory metals or plastics, gas or liquid inflated balloons, micromuscles, pneumatic artificial muscles, or muscular thin films.

Micromuscle™ devices include an electroactive polymer (EAP), a class of conducting polymers that can be electrically controlled to produce a swelling and contracting motion similar to human muscle, and in this case could be used to expand the airway. For example, voltage applied to electroactive polymers, including ionic polymer metal composites, causes flexion or form a curved open shape, which in this case would be designed to stent open the airway.

Some artificial muscles use flexible, ever-more ubiquitous carbon nanotubes as electrodes instead of other films.

Pneumatic artificial muscles could be used in a expandable biasing member, introducing air through a tube to cause a small mechanism to expand or contract.

Muscular thin films (MTFs) are formed by growing heart muscle cells from rats onto flexible plastic strips. These centimeter-scale MTFs could eventually be used in engineered devices of all sizes. Electrical impulses can be used to make the muscle fibers contract, causing the MTFs to roll up and potentially grip objects. After the initial contraction, the muscle relaxes and the flexible plastic helps the muscle fibers to return to their original position. This pattern of contraction and relaxation can be controlled, or paced, leading to more diverse functions, in this case stenting open the airway.

Figure 22A:
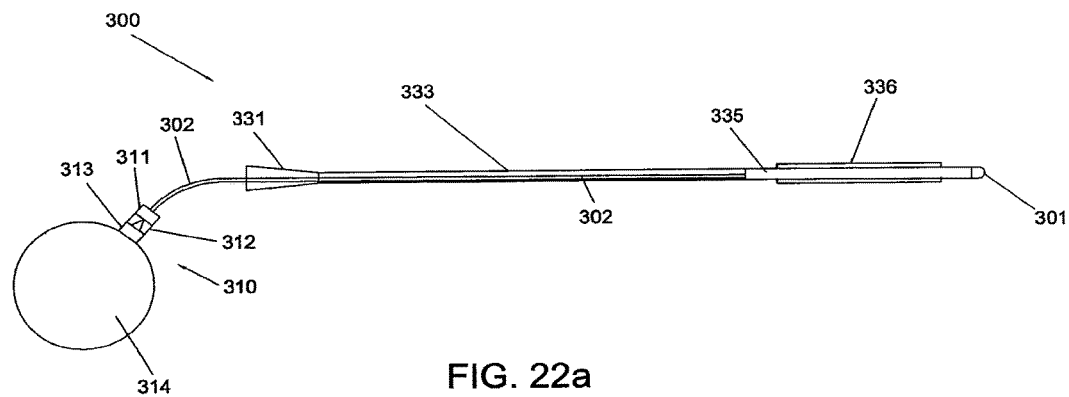
FIG. 22a is a side sectional view of a nasally inserted appliance according to one embodiment of the present disclosure, wherein the appliance is in an unexpanded state and includes a multi-lobed balloon surrounded by a compliant tube and attached to a fill assembly.

Referring now to FIGS. 22 a, 22 b and 22 c, a nasally inserted appliance of the present invention is illustrated, including a biasing member comprising a multi-lobed balloon, a membrane configured to maintain a smooth surface when the balloon is deflated, and a removable fill assembly configured to expand the balloon. Appliance 300 includes elongate nasal tube 333 configured to be inserted into a nostril of the patient. The nasal tube 333 includes a distal tip 301. At the proximal end of nasal tube 333 is nose cone 331 configured to frictionally engage and/or apply a radial force upon the nostril of the patient. Near the distal end of tube 333 is a biasing member of the present invention, multi-lobed balloon 335, which is surrounded by a compliant sleeve, membrane 336, which is resiliently biased in the minimal diameter geometry shown in FIG. 22 a. Appliance 300 is configured such that the outer surface of membrane 336 is smooth both when balloon 335 is inflated as shown in FIG. 22 b, or deflated as shown in FIG. 22 a. This smooth surface improves the comfort to the patient during insertion and removal of nasal tube 333 from the patient's airway, such as by covering one or more folds that may be present in balloon 335 when balloon 335 is deflated, and/or by including one or more friction reduced surfaces, such as a Teflon surface, a hydrophilic coating, a hydrophobic coating, or combinations of these.

Appliance 300 further includes a fill assembly 310 which is in fluid communication with balloon 335 via inflation lumen 302, also referred to as a "tube lumen." Lumen 302 is fluidly attached to port 311 which is removably attached to the distal end of valve 312, typically a duck-bill, spring-activated or other one-way fluid valve. The proximal end of valve 312 is fluidly connected to the distal end of port 313 which is fluidly attached to a flexible pouch such as a silicone pouch, fill chamber 314. Fill chamber 314 is filled with one or more liquids or gases, such as room air. Fill chamber 314 may include one or more resilient ribs configured to maintain fill chamber 314 is an expanded state, such as to cause fill chamber 314 to automatically fill with room air when fill chamber 314 is unattached.

Figure 22B:
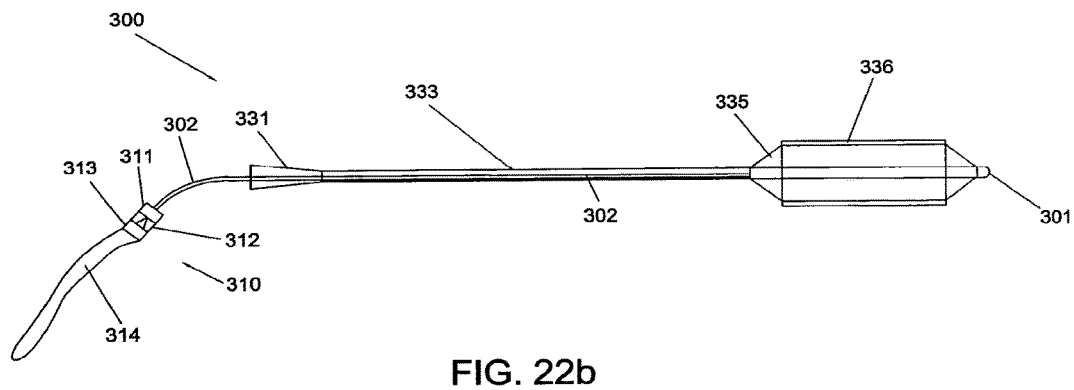
FIG. 22b is a side sectional view of the appliance of FIG. 22a, wherein the appliance is in an expanded state.

When a compressing force is applied to fill chamber 314, such as by the patient squeezing fill chamber 314, the liquids and/or gases pass through valve 312, through port 311 and inflation lumen 302 into balloon 335, such that balloon 335 expands, overcoming the applied compression force of membrane 336, as is shown in FIG. 22b. Valve 312 is configured such that when fill chamber 314 and port 313 are removed from valve 312, balloon 335 remains in an expanded state. When valve 312 is removed, balloon 335 is compressed due to the applied force of membrane 336, with the expanding fluid exiting via inflation lumen 302. In an alternative embodiment, valve 312 may be configured to be opened or otherwise deactivated to deflate balloon 335, avoiding the need for removing valve 312.

Figure 22C:
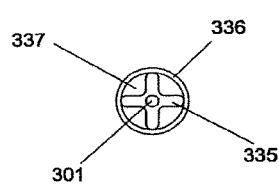
FIG. 22c is an end view of the appliance of FIG. 22a, with the multi-lobed balloon in the expanded state of FIG. 22b.

Referring specifically to FIG. 22c, balloon 335 is shown in the expanded state of FIG. 22b, wherein membrane 336 has also been expanded about balloon 335. The four lobes of balloon 335 are configured to create a passageway between each lobe, lumens 337, such that while membrane 336 circumferentially contacts the space behind the patient's soft palate or base of tongue, air can freely flow through lumens 337. In an alternative embodiment, balloon 335 may be included in appliance 300 without membrane 336, such that the tips of each lobe are the only points of contact with the internal surface of the patient's airway. In this particular configuration, balloon 335 may be deflated by applying a vacuum to port 311, with valve 312 removed or otherwise deactivated.

While we have shown and described several embodiments in accordance with our invention, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A medical appliance for a patient comprising:
 a nasal tube configured for insertion into a nasal passage of the patient;
 a biasing member disposed about a distal portion of said nasal tube, wherein said biasing member is configured to receive a volume of fluid to expand said biasing member to exert a force upon a soft palate and/or base of a tongue of said patient, wherein the biasing member includes a multi-lobed balloon;
 a membrane about the lobes of the multi-lobed balloon, wherein lumens between the lobes of the multi-lobed balloon and the membrane provide a passageway for a flow of air, and wherein the membrane is resiliently biased in a collapsed state, and wherein the membrane transitions to an expanded state when the biasing member receives the volume of fluid;
 a valve positioned proximal to said biasing member; and
 a tube lumen disposed between said valve and said biasing member,
 wherein said valve being in fluid communication with said biasing member,
 wherein said valve is positioned to receive the volume of fluid prior to said biasing member receiving the volume of fluid,
 wherein said valve is capable of maintaining said biasing member in an expanded state,
 wherein the membrane applies a compression force against the multi-lobed balloon,
 wherein a flow of the volume of fluid expands the multi-lobed balloon by overcoming the compression force applied by the membrane, and
 wherein the multi-lobed balloon is compressed by the applied compression force of the membrane when the valve is opened, removed, or deactivated.

2. The appliance according to claim 1, further comprising a fill assembly connected to and in fluid communication with said valve.

3. The appliance according to claim 2, wherein the fill assembly is removably attached to the valve.

4. The appliance according to claim 2, wherein said fill assembly comprises a fluid selected from the group consisting of: a liquid and a gas.

5. The appliance according to claim 1, wherein flow of fluid through said valve at least one of expands, contracts, or maintains a size of said biasing member.

6. The appliance according to claim 1, wherein said valve is selected from the group consisting of: a duck-bill valve; a spring-activated valve; and a one-way fluid valve.

7. The appliance according to claim 1, wherein said valve is configured to be opened to cause said biasing member to deflate.

8. The appliance according to claim 1, further comprising a nose cone at a proximal end of said nasal tube.

* * * * *